(12) United States Patent
Brown et al.

(10) Patent No.: US 6,623,724 B2
(45) Date of Patent: *Sep. 23, 2003

(54) DERMATOLOGICAL COMPOSITIONS AND METHODS

(75) Inventors: David A. Brown, Ellicott City, MD (US); Alexander A. Khorlin, Rockville, MD (US); Krystyna Lesiak, Gaithersburg, MD (US); Wu Yun Ren, Germantown, MD (US)

(73) Assignee: Applied Genetics Incorporated Dermatics, Freeport, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 198 days.

(21) Appl. No.: 09/085,917

(22) Filed: May 28, 1998

(65) Prior Publication Data

US 2002/0141952 A1 Oct. 3, 2002

Related U.S. Application Data

(63) Continuation-in-part of application No. PCT/US98/05346, filed on Mar. 18, 1998, now abandoned, which is a continuation-in-part of application No. PCT/US97/16642, filed on Sep. 18, 1997, which is a continuation-in-part of application No. 08/933,143, filed on Sep. 18, 1997.

(60) Provisional application No. 60/026,577, filed on Sep. 18, 1996, provisional application No. 60/035,947, filed on Jan. 21, 1997, provisional application No. 60/036,863, filed on Feb. 4, 1997, and provisional application No. 60/048,597, filed on Jun. 4, 1997.

(51) Int. Cl.$^7$ ................................................ A61K 7/42
(52) U.S. Cl. .................... 424/59; 514/183; 514/210; 514/211; 514/218; 514/222.2; 514/228.8; 514/277; 514/430; 514/449; 514/475; 514/506; 514/579; 514/663; 514/665; 514/667; 514/668; 514/670; 514/706; 514/716; 514/723; 514/762; 514/763; 514/764; 514/765; 514/766
(58) Field of Search ................................ 514/183, 210, 514/211, 218, 222.2, 228.8, 277, 430, 449, 475, 506, 579, 663, 665, 667, 668, 670, 706, 715, 716, 723, 762, 763, 764, 765, 766; 424/59

(56) References Cited

U.S. PATENT DOCUMENTS

| | | |
|---|---|---|
| 3,956,361 A | 5/1976 | Stephen |
| 4,102,995 A | 7/1978 | Hebborn |
| 4,104,203 A | 8/1978 | Hall et al. |
| 4,390,532 A | 6/1983 | Stüttgen et al. |
| 4,528,126 A | 7/1985 | Bruns et al. |
| 4,647,585 A | 3/1987 | Loots et al. |
| 5,041,485 A | 8/1991 | Eichenauer et al. |
| 5,068,453 A | 11/1991 | Kuwahara et al. |
| 5,130,136 A | 7/1992 | Shono et al. |
| 5,232,688 A | 8/1993 | Ziegler et al. |
| 5,302,378 A | 4/1994 | Crotty et al. |
| 5,352,440 A * | 10/1994 | Gilchrest et al. .............. 424/59 |
| 5,414,019 A | 5/1995 | Gould et al. |
| 5,532,001 A | 7/1996 | Gilchrest et al. |
| 5,554,359 A | 9/1996 | Fuller |
| 5,574,195 A | 11/1996 | Chastain et al. |
| 5,587,402 A | 12/1996 | Gould et al. |
| 5,591,423 A * | 1/1997 | Fuller .......................... 429/59 |
| 5,602,184 A | 2/1997 | Myers et al. |
| 5,626,839 A | 5/1997 | Scales-Medeiros |
| 5,698,184 A * | 12/1997 | Pickart ........................ 424/59 |
| 5,700,450 A | 12/1997 | Gilchrest et al. |
| 5,990,177 A | 11/1999 | Brown |
| 6,214,888 B1 | 4/2001 | Ren et al. |
| 6,231,837 B1 | 5/2001 | Stroud et al. |
| 6,267,948 B1 | 7/2001 | Ren et al. |
| 6,294,585 B1 | 9/2001 | Brown |

FOREIGN PATENT DOCUMENTS

| | | |
|---|---|---|
| EP | 0 643 113 | 3/1995 |
| GB | 1 200 862 | 8/1970 |
| WO | WO 87 04617 | 7/1987 |
| WO | WO 89 00853 | 2/1989 |
| WO | WO 96 09810 | 4/1996 |
| WO | WO 96/26711 | 9/1996 |
| WO | WO 97 03170 | 1/1997 |
| WO | WO 97 30692 | 8/1997 |
| WO | WO 98/11882 | 3/1998 |
| WO | WO 98 55085 | 12/1998 |
| WO | WO 99 08654 | 2/1999 |

OTHER PUBLICATIONS

Barthelman et al., "Inhibitory Effects of Perillyl Alcohol on UVB–induced Murine Skin Cancer and AP–1 Transactivation," *Cancer Research*, 1998, 58:711–716.

Brown et al., Aliphatic and Alicyclic Diols Induce Melanogenesis in Cultured Cells and Guinea Pig Skin, "Journal of Investigative Dermatology," 1998, 110:428–437.

Buchbauer et al., "Norbornanaverbindungen in der pharmazeutischen Forschung," *Pharmazie*, 1991, 46(Teil 1):88–97, and 46 (Teil 2):116–170.

Crowell et al., "Chemoprevention of mammary carcinogenesis by hydroxylated derivatives of d–limonene," *Carcinogenesis*, 1992, 13:1261–1264.

Crowell et al., "Structure–activity relationships among monoterpene inhibitors of protein isoprenylation and cell proliferation," *Biochemical Pharmacology*, 1994, 47:1405–1415.

Haag et al., "Mammary carcinoma regression induced by perillyl alcohol, a hydroxilated analog of limonene," *Cancer Chemotherapy and Pharmacology*, 1994, 34:477–483.

(List continued on next page.)

*Primary Examiner*—Nathan M. Nutter
(74) *Attorney, Agent, or Firm*—Maurice M. Klee

(57) ABSTRACT

Disclosed are methods and compositions for regulating the melanin content of mammalian melanocytes; regulating pigmentation in mammalian skin, hair, wool or fur; treating or preventing various skin and proliferative disorders; by administration of various compounds, including alcohols, diodls and/or triols and their analogues.

41 Claims, 6 Drawing Sheets

OTHER PUBLICATIONS

He et al., "Isoprenoids Suppress the Growth of Murine B16 Melanomas In Vitro and In Vivo," *J. Nutr.*, 1997, 127:668–674.

Jager et al., "Investigation of cytotoxic effects of 8 norbornane derivatives on 4 human cancer cell lines using the MTT assay," *Pharmazie*, 1995, 50:619–621.

Karlberg et al., "Hydroperoxides in oxidized d–limonene identified as potent contact allergens," *Arch. Dermatol. Res.*, 1994, 286:97–103.

Kitahara et al., "Evaluation of Skin Damage of Cyclic Monoterpenes, Percutaneous Absorption Enhancers, by Using Cultured Human Skin Cells," *Biol. Pharm. Bull.*, 1993, 16:912–916.

Ohmori et al., "Pharmacological Regulation on Melanogenesis," *Nippon Koshohin Kagakkaishi*, 1994, 18:215–219. English translation attached[1].

Romero et al., "Involvement of Nitric Oxide and Cyclic GMP in Melanogenesis of Human Melanocytes," *J. Invest. Dermatol.*, 1996, 106:886.

Russin et al., "Inhibition of rat mammary carcinogenesis by monoterpenoids," *Carcinogenesis*, 1989, 10:2161–2164.

Shi et al., "Induction of differentiation in neuro–2A cells by the monoterpene perillyl alcohol," *Cancer Letters 95*, 1995, 1–6.

Shoff et al., "Concentration–dependent Increase of Murine P388 and B16 Population Doubling Time by the Acyclic Monoterpene Geraniol," *Cancer Research*, 1991, 41:37–42.

Abdel–Malek et al., "Mitogenic, Melanogenic, and cAMP Responses of Cultured Neonatal Human Melanocytes to Commonly Used Mitogens," *J. Cell. Physiol.*, 1992, 150:416–425.

Allan et al., "Topically Applied Diacylglycerols Increase Pigmentation in Guinea Pig Skin," *J. Invest. Dermatol.*, 1995, 105:687–692.

Baudouin et al., "Constitutive Nitric Oxide Synthase Is Present in Normal Human Keratinocytes," *J. Invest. Dermatol.*, 1996, 106:428–431.

Bradford, M. "A Rapid and Sensitive Method for the Quantitation of Microgram Quantities of Protein Utilizing the Principle of Protein–Dye Binding," *Anal. Biochem.*, 1967, 72:248–254.

Buchbauer et al., "Syntheses in the isocamphane series," *Chemical Abstracts*, vol. 95, No. 115756e, 1981.

Carsberg et al., "Ultraviolet radiation–induced melanogenesis in human melanocytes," *J. Cell. Sci.*, 1994, 107:2591–2597.

Chijiwa et al., "Inhibition of Forskolin–induced Neurite Outgrowth and Protein Phosphorylation by a Newly Synthesized Selective Inhibitor of Cyclic AMP–dependent Protein Kinase, N–[2–(p–Bromocinnamyl–amino)ethyl]–5–isoquinolinesulfonamide (H–89), of PC12D Pheochromocytoma Cells," *J. Biol. Chem.*, 1990, 265:5267–5272.

Cieszka et al., "Growth and pigmentation in genetically related Cloudman S91 melanoma cell lines treated with 3–isobutyl–1–methyl–xanthine and β–melanocyte–stimulating hormone," *Exp. Dermatol.*, 1995, 4:192–198.

Eller et al., "DNA damage enhances melanogenesis," *Proc. Natl. Acad. Sci.*, 1996, 93:1087–1092.

Friedmann et al., "Ultraviolet Radiation Directly Induces Pigment Production by Cultured Human Melanocytes," *J. Cell. Physiol.*, 1987,133:88–94.

Fuller et al., "Hormonal Regulation of Melanogenesis in Mouse Melanoma and in Human Melanocytes," *Ann. NY Acad. Sci.*, 1993, 690:302–319.

Fuller et al., "Regulation of Tyrosinase in Mouse Melanoma Cells and in Human Melanocytes by PKC and PKA Pathways," *Pigment Cell Res.*, 26th International Pigment Cell Conference Abstacts, 1996, S5:65.

Garvey et al., "Potent and Selective Inhibition of Human Nitric Oxide Synthases," *J. Biol. Chem.*, 1994, 269:26669–26676.

Gates et al., "Comparison of skin color with melanin content," *J. Invest. Dermatol.*, 1953, 21:339–348.

Gilcrest et al., "Mechanisms of Ultraviolet Light–Induced Pigmentation," *Photochem. Photobiol.*, 1996, 63:1–10.

Hidaka et al., "Isoquinolinesulfonamides, Novel and Potent Inhibitors of Cyclic Nucleotide Dependent Protein Kinase and Protein Kinase C," *Biochemistry*, 1984, 23, 5036–4041.

*Introduction to the Cellular and Molecular Biology of Cancer*, L. M. Franks and T. Teich, 1987, Oxford University Press.

Ishida et al., "Biotransformation of terpenoids in mammals," *Chemical Abstracts*, vol. 93, #89860w, 1980.

Jara et al., "Assays for Mammalian Tyrosinase: A Comparative Study," *Pigment Cell Res.*, 1988, 1:332–339.

Jimbow et al., "Biology of Melanocytes" in *Dermatology in General Medicine*, 4th edition, eds: Fitzpatrick et al., McGraw–Hill, New York, 1993, vol. 1, pp. 261–289.

Kamikubo et al., "Preparation of (+)–tricycloen–3–one and its conversion into (+)–epi–β–santalene," *Chemical Abstracts*, vol. 122, No. 265669u, 1994.

Karg et al., "Hydrogen Peroxide as a Mediator of Dopac–Induced Effects on Melanoma Cells," *J. Invest. Dermatol.*, 1991, 96:224–227.

Karg et al., "Hydrogen Peroxide as an Inducer of Elevated Tyrosinase Level in Melanoma Cells," *J. Invest. Dermatol.*, 1993, 100:209S–213S.

Karg et al., "Stimulation of Tyrosinase by Dihydroxy Phenyl Derivatives," *Acta Derm. Venereol.*, 1989, 69:521–524.

Koval'skaya et al., "Determination of the spatial structure of mono– and bicyclic terpene derivatives on the base of nuclear magnetic resonance spectroscopy data," *Chemical Abstracts*, vol. 125, No. 276201y, 1990.

Kozlov et al., "Camphene in the synthesis oxygen– and nitrogen–containing bicyclic derivatives," *Chemical Abstracts*, vol. 120, No. 77469p, 1994.

Laukharanta et al., "Changes in Three–Dimensional Structure of Cultured S91 Mouse Melanoma Cells Associated with Growth Inhibition and Induction of Melanogenesis by Retinoids," *Arch. Dermatol. Res.*, 1985, 277:147–150.

McLane et al., "Phosphorylated Isomers of L–dopa Stimulate MSH Binding Capacity and Responsiveness to MSH in Cultured Melanoma Cells," *Biochem. Biophys. Res. Commun.*, 1987, 145:719–725.

Merkel, D. "10–Methylenetricyclene," *Chemical Abstracts*, vol. 66, No. 94723a, 1967.

Miftakhov et al., "Prostanoids," *Chemical Abstracts*, vol. 121, No. 157329d, 1994.

Miles et al., "Fluorometric Determination of Nitric Oxide," *Methods*, 1995, 7:40–47.

Moshage et al., "Nitrite and Nitrate Determinations in Plasma: A Critical Evaluation," *Clin. Chem.*, 1995, 41:892–896.

Orlow et al., "Inhibition of Induced Melanogenesis in Cloudman Melanoma Cells by Four Phenotypic Modifiers," *Exp. Cell Res.,* 1990, 191:209–218.

Pomerantz, S. H., "The Tyrosine Hydroxylase Activity of Mammalian Tyrosinase," *J. Biol. Chem.,* 1966, 241:161–168.

Romero et al., "Retinoic acid as modulator of UVB–induced melanocyte differentiation," *J. Cell Sci.,* 1994, 107:1095–1103,.

Romero–Graillet et al., "Nitric Oxide Produced by Ultraviolet–irradiated Keratinocytes Stimulates Melanogenesis," *J. Clin. Invest.,* 1997, 99:635–642.

Romero–Graillet et al., "Ultraviolet B Radiation Acts through the Nitric Oxide and cGMP Signal Transduction Pathway to Stimulate Melanogenesis in Human Melanocytes," *J. Biol. Chem.* 1996, 271:28052–28056.

Schmidt et al., "Determination of Nitric Oxide via Measurement of Nitrite and Nitrate in Culture Media," 1995, *Biochemica* 2:22.

Siracký et al., "Relationship between melanogenesis, proliferative activity and response to chemotherapy of human melanoma xenografts," *Neoplasia,* 1984, 31:545–549,.

Southan et al., "Isothioureas: potent inhibitors of nitric oxide synthase with variable isoform selectivity," *Br. J. Pharmacol.,* 1995, 114:510–516.

Toullec et al., "The Bisinodylmaleimide GF 109203X is a Potent and Selective Inhibitor of Protein Kinase C," *J. Biol. Chem.,* 1991, 266:15771–15781.

Uçar, K., "The effects of histamine H2 receptor antagonists on melanogenesis and cellular proliferation in melanoma cells in culture," *Biochem. Biophys. Res. Commun.,* 1991, 177:545–550.

Uchida et al., "Electrochemical oxidation of polycyclic cyclopropanes and camphene," *Chemical Abstracts,* vol. 112, No. 198816t, 1990.

Wintzen et al., "Proopiomelanocortin, Its Derived Peptides, and the Skin," *J. Invest. Dermatol.,* 1996, 106:3–10.

Hasenfratz "Experience in the treatment of acne vulgaris with the preparation acne–medice," *Asthetische Medizin,* 15:206–208, 1966.

\* cited by examiner

DERMATOLOGICAL COMPOSITIONS AND METHODS

CROSS REFERENCE TO RELATED APPLICATIONS

This application is a continuation-in-part off. PCT/US98/05346 filed Mar. 18, 1998 and now abandoned, which is a continuation-in-part of PCT/US97/16642 filed Sep. 18, 1997, which is a continuation-in-part of application Ser. No. 08/933,143 filed Sep. 18, 1997, which is a continuation-in-part of application Ser. No. 60/026,577 filed Sep. 18, 1996, of application Ser. No. 60/035,947 filed Jan. 21, 1997, of application Ser. No. 60/036,863 filed Feb. 4, 1997, and of application Ser. No. 60/048,597 filed Jun. 4, 1997.

STATEMENT REGARDING FEDERALLY SPONSORED RESEARCH OR DEVELOPMENT

Not Applicable

BACKGROUND OF THE INVENTION

1. Field of the Invention

The present invention relates to regulating the melanin content of mammalian melanocytes; regulating pigmentation in mammalian skin, hair, wool or fur; restoring pigmentation to grey hair; treating or preventing various skin and proliferative disorders; by administration of various compounds, including alcohols, diols and/or triols and their analogues.

2. Description of Related Art

U.S. Pat. No. 5,352,440 is directed to increasing melanin synthesis in melanocytes and increasing pigmentation by administration of certain diacylglycerol compounds.

U.S. Pat. No. 5,532,001 is directed to increasing pigmentation in mammalian skin via administration of certain DNA fragments.

U.S. Pat. No. 5,554,359 is directed to increasing levels of melanin in melanocytes by administration of lysosomotropic agents.

SUMMARY OF THE INVENTION

The present invention provides a method for increasing the melanin content of mammalian melanocytes, which comprises administering to said melanocytes an effective amount of a $C_3$–$C_{50}$ diol, which may be aliphatic or aromatic, linear, branched, mono-, bi- or polyclicic, saturated or unsaturated, unsubstituted, mono- or polysubstituted.

Another aspect of the present invention concerns a method for increasing or restoring pigmentation in mammalian skin, hair or wool, which comprises administering to said mammal an effective amount of one or more compounds described above.

Another aspect of the present invention concerns a method for treating a skin proliferative disorder or a disorder of keratinization in a mammal, which comprises administering to a mammal in need of such treatment an effective amount of one or more compounds described above.

A further aspect of the present invention concerns a method for preventing a skin proliferative disorder or a disorder of keratinization in a mammal, which comprises administering to a mammal in need of such preventive treatment an effective amount of one or more compounds described above.

An additional aspect of the present invention concerns a method for treating a tumorous or cancerous disorder whereby application of one or more of the compounds described above results in reversal of said disorder by virtue of induction of differentiation of cancerous or tumorous cells to a less- or non-proliferative phenotype. These cancerous or tumorous disorders include, but are not limited to, proliferative disorders of a dermatological nature.

In another aspect, the present invention provides a composition for increasing the melanin content of mammalian melanocytes, which comprises:

a) an effective amount of one or more compounds described above; and b) a suitable carrier.

In another aspect, the present invention provides a composition for treating a skin proliferative disorder or a disorder of keratinization, which comprises:

a) an effective amount of one or more compounds described above; and b) a suitable carrier.

In yet another aspect, the present invention provides a composition for preventing a skin proliferative disorder, which comprises:

a) an effective amount of one or more compounds described above; and b) a suitable carrier.

The present invention additionally provides a method for increasing the melanin content of mammalian melanocytes, which comprises administering to said melanocytes an effective amount of one or more compounds having the following structure:

wherein
   each X is independently selected from a single or double bond; or a group containing from one atom to twenty atoms, at least one of which is carbon, nitrogen, oxygen or sulfur;
   each $R_1$ is independently selected from hydrogen; halogen; an acyl or amino acyl group containing from one atom to twenty atoms, at least one of which is carbon, nitrogen, oxygen, or sulfur; or a group containing from one atom to twenty atoms, one of which is carbon, nitrogen, oxygen, or sulfur;

$R_2$ is a linear, branched or unbranched, cyclic, bicyclic or polycyclic group containing from one atom to fifty atoms, at least one of which is carbon, nitrogen, oxygen, or sulfur; and each R is independently selected from $R_1$; $R_2$; hydroxyl, methyl, hydroxymethyl, —$(CH_2)_n CH_3$—, —$(CH_2)_n OH$, —$(CH_2)_n OR_1$, —$(CH_2)_n$—CH(OH)—CHOH, —$(CH_2)_n$—CH(OH)—CH(OH)$R_1$, —$(CH_2)_n$—CH(OH)—$(CH_2)_n$—$CH_2$(OH), —$(CH_2)_n$—CH(OH)—$(CH_2)_n$—CH(OH)$R_1$ or —$CH_2 OR_1$, wherein each n is independently an integer from 0–25;

and pharmaceutically acceptable salts or prodrugs thereof, with the proviso that with reference to the first listed structure only, when the X to which $R_1$ is attached is a single bond and each R is acyl and one of $R_1$ is hydroxymethyl (HOCH$_2$—), then the sum of carbon atoms in $R_1$ is greater than one.

Another aspect of the present invention concerns a method for increasing or restoring pigmentation in mammalian skin, hair or wool, which comprises administering to said mammal an effective amount of one or more compounds depicted above.

Another aspect of the present invention concerns a method for treating a skin proliferative disorder or a disorder of keratinization in a mammal, which comprises administering to a mammal in need of such treatment an effective amount of one or more compounds depicted above.

A further aspect of the present invention concerns a method for preventing a skin proliferative disorder or a disorder of keratinization in a mammal, which comprises administering to a mammal in need of such preventive treatment an effective amount of one or more compounds depicted above.

An additional aspect of the present invention concerns a method for treating a tumorous or cancerous disorder whereby application of one or more of the compounds depicted above results in reversal of said disorder by virtue of induction of differentiation of cancerous or tumorous cells to a less- or non-proliferative phenotype. These cancerous or tumorous disorders include, but are not limited to, proliferative disorders of a dermatological nature.

In another aspect, the present invention provides a composition for increasing the melanin content of mammalian melanocytes, which comprises:

a) an effective amount of one or more compounds depicted above; and b) a suitable carrier.

In another aspect, the present invention provides a composition for treating a skin proliferative disorder or a disorder of keratinization, which comprises:

a) an effective amount of one or more compounds depicted above; and b) a suitable carrier.

In yet another aspect, the present invention provides a composition for preventing a skin proliferative disorder, which comprises:

a) an effective amount of one or more compounds depicted above; and b) a suitable carrier.

In yet another aspect, the present invention provides a method of altering or restoring pigmentation in mammalian skin, hair, wool or fur, which comprises administering to a mammal an effective amount of a compound which alters cellular production of nitric oxide, wherein an increase in nitric oxide production results in increased pigmentation, and a decrease in nitric oxide production results in decreased pigmentation.

In yet another aspect, the present invention provides a method of altering pigmentation in mammalian skin, hair, wool or fur, which comprises administering to a mammal an effective amount of a compound which alters cellular production of cyclic guanosine monophosphate, wherein an increase in cyclic guanosine monophosphate production results in increased pigmentation, and a decrease in cyclic guanosine monophosphate production results in decreased pigmentation.

In yet another aspect, the present invention provides a method of altering pigmentation in mammalian skin, hair, wool or fur, which comprises administering to a mammal an effective amount of a compound which alters cellular activity of protein kinase G, wherein an increase in protein kinase G activity results in increased pigmentation, and a decrease in protein kinase G activity results in decreased pigmentation.

In yet another aspect, the present invention provides a method of identifying a substance which alters pigmentation in mammalian melanocytes, which comprises evaluating the effect the substance has on cellular production of nitric oxide, wherein if such production is altered, then the pigmentation in mammalian melanocytes is altered.

In yet another aspect, the present invention provides a method of identifying a substance which alters pigmentation in mammalian melanocytes, which comprises evaluating the effect the substance has on cellular production of cyclic guanosine monophosphate, wherein if such production is altered, then the pigmentation in mammalian epidermal melanocytes is altered.

In yet another aspect, the present invention provides a method of identifying a substance which alters pigmentation in mammalian melanocytes, which comprises evaluating the effect the substance has on cellular activity of protein kinase G, wherein if such activity is altered, then the pigmentation in mammalian epidermal melanocytes is altered.

DETAILED DESCRIPTION OF THE INVENTION

Figure 1A:
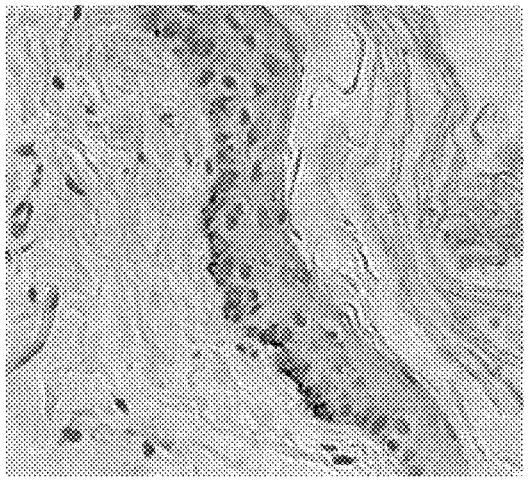
FIGS. 1A–1D are printouts from an Oncor. Imaging System™ of Fontana-Masson stained guinea pig skin biopsy samples as described in Example 5.
Figure 1B:
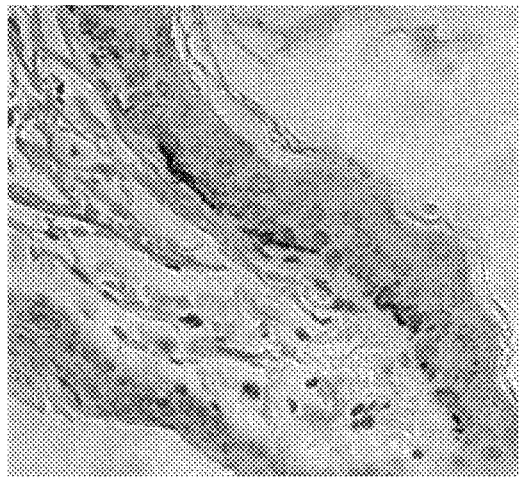

The present invention is based on the unique observation that certain compounds effectively and efficiently induce melanogenesis in mammalian cells, which has several consequences. First, increasing melanogenesis leads to increasing the melanin content of melanocytes, and hence results in increased pigmentation or darkened color of the skin, hair wool or fur. Thus, the present invention is useful in the treatment of hypopigmentation disorders, such as albinism, vitiligo, etc. It is also believed that increasing the pigmentation of skin according to the present invention will protect such skin from subsequent UV light damage, sunburn, photoaging and development of skin cancers. Finally, since the methods and compositions described herein induce differentiation of a melanoma cell line, the present invention may be used to treat hyperproliferative disorders such as actinic keratosis, basal cell carcinoma, squamous cell carcinoma, fibrous histiocytoma, dermatofibrosarcoma protuberans, hemangioma, nevus flammeus, xanthoma, Kaposi's sarcoma, mastocytosis, mycosis fungoides, lentigo, nevocellular nevus, lentigo maligna, malignant melanoma, and metastatic carcinoma.

The present methods and compositions are also useful in the treatment of diseases characterized by inflammation and disturbance of keratinization, including psoriasis vulgaris, psoriasis eosinophilia, acne vulgaris, acne conglobata, acne fulminans, osteoma cutis, nodulocystic acne, cystic acne and benign and premalignant dermatoses.

The active compounds according to the present invention are the $C_3$–$C_{50}$ diols described above (by "diol" is meant a compound which has at least two, but permissibly more, -OH groups). Preferably, the active have one of the six structures depicted above. More preferably, X is independently selected from a single bond; or $C_1$–$C_{10}$ alkylene, $C_2$–$C_{10}$ alkenylene, or $C_2$–$C_{10}$ alkynylene, each of which may contain one or more different heteroatoms or heteroatoms of the same type. More preferably each $R_1$ is independently selected from hydrogen; fluoro; chloro; or $C_1$–$C_{20}$ alkyl, $C_2$–$C_{20}$ alkenyl, $C_2$–$C_{20}$ alkynyl, $C_7$–$C_{20}$ aralkyl, $C_8$–$C_{20}$ aralkenyl, $C_8$–$C_{20}$ aralkinyl, or $C_6$–$C_{20}$ aryl, each of which may contain one or more different heteroatoms or heteroatoms of the same type, or carboxyl, carboxamido, carbalkoxy, sulfamido, sulfonamido; hydroxyl, or amino. More preferably $R_2$ contains from two to twenty carbon atoms, each may contain one or more different heteroatoms or heteroatoms of the same type.

The preparation of the present compounds would be apparent to one of ordinary skill, and many of them are commercially available. Representative preferred compounds include, but are not limited to:

1,2-Ethanediol
1,2-Propanediol (Propylene Glycol)
(S)-(+)-1,2-Propanediol [(S)-(+)-1,2-Propylene Glycol]
1,3-Propanediol
2,3-Dimethyl-2,3-Butanediol
2,3-Dimethyl-1,2-Butanediol
1-Phenyl-1,2-Propanediol
2-Methyl-1,3-Propanediol
1,2-Butanediol
1,3-Butanediol
1,4-Butanediol
2,3-Butanediol
(2R,3R)-(−)-2,3-Butanediol
(2S,3S)-(+)-2,3-Butanediol
2,3-meso-Butanediol
1,2-Pentanediol
1,4-Pentanediol
1,5-Pentanediol
2,4-Pentanediol
1,2-cis-cyclopentanediol
1,2-trans-cyclopentanediol
1,2-cis-cyclohexaneanediol
1,2-trans-cyclohexanediol
1,2-dihydroxy-4,5-cyclohexanediol carbonate
1,2,4,5-tetrahydroxycyclohexane
1,2-Hexanediol
1,5-Hexanediol
1,6-Hexanediol
2,5-Hexanediol
1,2-Heptanediol
1,7-Heptanediol
7-Octene-1,2-diol
1,2-Octanediol
1,8-Octanediol
1,2-Nonanediol
1,9-Nonanediol
1,2-Decanediol
1,10-Decanediol
1,2-Dodecanediol
1,12-Dodecanediol
1,2-Tetradecanediol
1,14-Tetradecanediol
1,2-Hexadecanediol
1,16-Hexadecanediol
Glycerol
1,2,4-Butanetriol
1,2,3-Trihydroxyhexane
1,2,6-Trihydroxyhexane
1,2,3-Heptanetriol
β-estradiol
azabicyclo-(2,2,1)-heptanediol-3-one
1,4-dioxane-2,3-diol
5-norbornene-2,2-dimethanol
norbornane-2,2-dimethanol
2,3-norbornanediol (exo or endo or cis or trans)
2,3-cis-exo-norbornanediol
α-norborneol
2-norbornanemethanol
norbornane
borneol
camphor
camphene
camphane
norbornane acetic acid
norbornane-carboxylic acid
norbornane-dicarboxylic acid
2-endo-hexadecylamino-5-norbornene-2-exo-methanol
2-endo-hexadecylamino-5-norbornene-2,3-exo-dimethanol
2-(propyl-1,2-diol)-norbornane
1,2-dithiane-trans-4,5-diol
2,3-pyridinediol
2,3-pyridinediol hydrogen chloride
2,3-pyridinediol glycolic acid
2,3-dipyridyl-2,3-butanediol
2,2,4,4-tetramethyl-1,3-cyclobutanediol
norborneol
2,7-norbornanediol 2,5,7-norbornanetriol
2,6,7-norbornanetriol
2-hydroxy-2-norbornanemethanol
1-(exo-2-norbornyl-)-propan-1,2-diol
1-(endo-2-norbornyl-)-propan-1,2-diol
methyl-5-norbornene-2,3-dimethanol
4 2-norbornaneacetic acid
1,2-cis-cyclohexanedimethanol
3-cyclohexane-1,1-dimethanol
1,4-cyclohexanedimethanol
pentaerylthritol
pinane
pinaneol
2,3-cis/exo-pinanediol ([1R,2R,3S,5R]-[−]-pinanediol and [1S, 2S,3R,5S]-[+]-pinanediol])
(1R)-(−)-trans-pinane-1,10-diol
(1S,2S,5S,)-2-hydroxy-3-pinanone
(−)-isopinocampheol
(S)-cis-verbenol
bornane
borneol
2,3-cis/exo-bornanediol
2,3-trans-bornanediol
camphanediol
camphenediol
cis-p-menthane-3,8-diol
trans-p-menthane-3,8-diol
sobrerol (trans-p-meth-6-ene-2,8-diol)
αterpineol
terpinen-4-ol
(−)-cis-myrtanol [(1S,2R)-10-Pinanol]
(+)-trans-myrtanol [(1R,2R)-10-Pinanol]
(−)-trans-myrtanol [(1S,2S)-10-Pinanol]
(−)-myrtenal [(1R)-2-Pinen-10-al]
(−)-myrtenol [(1R)-2-Pinene-10-ol]
carveol [p-mentha-6,8-dien-2-one]
menthol Particularly preferred compounds of this invention are 2,3-cis/exo-pinanediol ([1R,2R,3S,5R]-[−]-pinanediol and [1S,2S,3R,5S]-[+]-pinanediol]; 2,3-cis/exo-bornanediol; 5-norbornene-2,2-dimethanol; norbornane-2,2-dimethanol; 2-hydroxy-2-norbornanemethanol; 1-(exo-2-norbornyl-)-propan-1,2-diol; and 1-(endo-2-norbornyl-)-propan-1,2-diol. Other preferred compounds are (1S,2S,5S,)-2-hydroxy-3-pinanone; 2,3-trans-pinanediol; (1R)-(−)-trans-pinane-1,10-diol; 2,3-trans-bornanediol; cis-p-menthane-3,8-diol; trans-p-menthane-3,8-diol; 1,2-cis-cyclopentanediol, 2,3-cis/exo-norbornanediol; 2-norbornanemethanol; (1R)-(−)-myrtenol, and 3,3-dimethyl-1,2-butanediol.

The methods and compositions of the present invention contemplate the use of one or more of the above-mentioned compounds as an active ingredient for various uses. In a preferred embodiment, the active ingredient(s) is combined with an acceptable carrier to form a topical formulation which may be placed on the skin for dermatological uses. Topical formulations may include ointments, lotions, pastes, creams, gels, drops, suppositories, sprays, liquids, shampoos, powders and transdermal patches. Thickeners, diluents, emulsifiers, dispersing aids or binders may be used as needed. Preferably, one function of the carrier is to enhance skin penetration of the active ingredient(s), and should be capable of delivering the active ingredient(s) to melanocytes under in vivo conditions. Suitable carriers are well known to one of ordinary skill, and include liposomes, ethanol, dimethylsulfoxide (DMSO), petroleum jelly (petrolatum), mineral oil (liquid petrolatum), water, dimethylformamide, dekaoxyethylene-oleylether, oleic acid, 2-pyrrolidone and Azone® brand penetration enhancer (Upjohn). A particularly preferred composition includes an active ingredient(s) as described above, with one of 2-pyrrolidone, oleic acid and/or Azone® as penetration enhancer, solubilized in a base of water, ethanol, propanol and/or propylene glycol (the latter component having properties of a carrier, penetration enhancer and an active ingredient as described herein). Depending on the specific application, the compositions of the present invention may also include other active ingredients, as well as inert or inactive ingredients.

Particularly preferred formulations include an active ingredient(s) in conjunction with one or more melanogenesis-enhancing agents such as α-hydroxy acids, salts and derivatives thereof; α-keto acids, salts and derivatives thereof; β-hydroxy acids, salts and derivatives thereof; retinoids, salts and derivatives thereof; Vitamin A and related compounds; acids; phenol; and methoxypropyl-gluconamide, as more fully described in co-pending application Serial No. 09/055,274 filed Apr. 6, 1998 entitled "Dermatological Formulations and Methods", the contents of which are incorporated herein by reference.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved, or a cosmetically desired degree of melanogenesis (tanning) is achieved, depending on the application. One of ordinary skill may readily determine optimum dosages, dosing methodologies and repetition rates. In general, it is contemplated that topical formulations (such as creams, lotions, solutions, etc.) will have a concentration of active ingredient of from about 0.01% to about 50%, preferably from about 0.1% to about 10%. In general, it is contemplated that unit dosage form compositions according to the present invention will contain from about 0.01 mg to about 100 mg of active ingredient, preferably about 0.1 mg to about 10 mg of active ingredient.

Another aspect of the present invention is based on the observation that the subject compounds which stimulate melanin production act via the Nitric Oxide/cyclic Guanosine monophosphate/Protein Kinase G ("NO/cGMP/PKG") pathway. Thus, the present invention includes not only the compounds described above, but any compound which acts via the NO/cGMP/PKG pathway to stimulate melanin synthesis by increasing cellular production of NO, cGMP or PKG. Conversely, agents which decrease cellular production of NO, cGMP or PKG will decrease or suppress melanin production and pigmentation in mammalian skin, hair, fur or wool, and the present invention is also directed to those compositions and methods. Such is useful in, for example, the lightening of skin, hair, wool or fur for cosmetic purposes, or the treatment of hyperpigmentation or uneven pigmentation disorders such as vitiligo, dermal melanocytosis, Franceschetti-Jadassohn Syndrome, etc. For such depigmentation applications, the formulation and dosing would be as described above with respect to pigmentation applications.

Discovery of the pathway through which the present compounds act also leads to methods for screening compounds for melanogenic activity and potency, or for their ability to reduce or suppress melanogenesis, based on measurement of generation of nitric oxide (NO) or measurement of nitric oxide synthesis (NOS) activity. Methods for measurement of NO or NOS include but are not limited to the following well known methods. Measurement of NO is usually based on the fact that NO rapidly decomposes to nitrate and nitrite in aqueous solution. Nitrate reductase is added to culture media or cell extracts to ensure complete conversion of nitrate to nitrite. Griess reagents (sulfanilamide and N-[1-naphthyl]-ethylenediamine) are then added to convert nitrite into a deep purple azo compound that absorbs maximally at 540 nm (Schmidt, et al., 1995, *Biochemica* 2:22). Reactions are typically carried out in a 96-well format with absorbances read on a microtiter plate reader. Alternatively, following conversion of nitrate to nitrite as described above, DAN reagent (2,3-diaminonaphthalene) is added followed by NaOH which converts nitrite into the fluorescent compound 1(H)-naphthotriazole. This is measured fluorimetrically with excitation at 365 nm and emission at 450 nm, typically in a 96-well format (Miles, et al., 1995, *Methods* 7:40). NOS activity is measured by adding [$^3$H]-arginine to intact tissues or protein extracts, and measuring release of $^3$H resulting from the conversion of arginine to citrulline during the enzymatic formation of NO by NOS (Baudouin and Tachon, 1996, *J. Invest. Dermatol.* 106:428–431). Alternatively, the production of cGMP or activity of PKG can be used as a screening tool. CGMP may be measured by commercially available immunoassay (see Romero-Graillet, et al., 1996, *J. Biol. Chem.* 271:28052–28056). PKG may be measured by cyclic GMP dependent kination of a primary histone target (see Hidaka, et al., *Biochemistry* 1984, 23, 5036–5041)

The use of and useful and novel features of the present methods and compositions will be further understood in view of the following non-limiting examples.

EXAMPLE 1

The Cloudman S91 mouse melanoma cell line was obtained from American Type Culture Collection (ATCC). Cells were cultured in Dulbecco's Modified Eagles Medium (DMEM) containing 10% calf serum, 2 mM L-glutamine, 10 U Penicillin/ml and 10 ug Streptomycin/ml according to a previously published protocol (Eller, et al., Proc. Natl. Acad. Sci. 93:1087–92. 1996). For testing propylene glycol and analogues for induction of melanogenesis, S91 cells were plated at $10^5$ cells/35 mm dish in 10% calf serum. One day after plating, media was removed and replaced with media containing 2% calf serum and test compounds (Eller, et al., 1996). Cells were cultured for 6 days at 37° C. in 5% $CO_2$ in a humidified incubator. Following this treatment period, cells were examined microscopically and the portion of dedifferentiated and differentiated cells was estimated. Previous studies have shown that dedifferentiated S91 cells have a rounded, spindly appearance while differentiated S91 cells have a flattened, cuboidal, multipolar and dendritic appearance (Orlow, et al., *Exp. Cell Res.* 191:209–218, 1990).

Following this microscopic examination, cells were detached from dishes by trypsin. The time required for detachment by trypsin was recorded as an additional indicator of the phenotypic effects of test compounds. For each treatment, a subsample of cells was counted to determine the effects of treatment compounds on cellular proliferation. The remainder of cells were used for determination of melanin content. Melanin was extracted from cells by vortexing for 15 min in 1N NaOH. Standards were prepared by dissolving melanin (Sigma) in 1 N NaOH (Eller, et al., 1996). Absorbance of standards and samples was measured at 475 nm. Melanin was expressed as pg melanin/cell.

Tables 1 and 2 below show the results obtained when testing formulations containing various concentrations of 1,2-propanediol as the active ingredient. In the control, no test compound was added to the medium.

TABLE 1

| Concentration | Cells (×10$^6$) | ug Melanin | pg Melanin/Cell |
|---|---|---|---|
| Control | 0.48 | 2.52 | 5.3 |
| 1% (136 mM) | 0.52 | 4.88 | 9.4 |
| 2% (272 mM) | o.50 | 6.24 | 12.5 |
| 3% (408 mM) | 0.20 | 4.03 | 20.2 |
| 4% (544 mM) | 0.10 | 4.01 | 40.1 |
| 5% (680 mM) | 0.08 | 2.31 | 28.9 |

TABLE 2

| Concentration | Morphology Rounded Spindly | Morphology Flattened Cuboidal | Trypsinization Detachment Time |
|---|---|---|---|
| Control | 100% | | ≦3 min |
| 1% (136 mM) | 90% | 10% | ≦6 min |
| 2% (272 mM) | 70% | 30% | ≦9 min |
| 3% (408 mM) | 40% | 60% | ≦12 min |
| 4% (544 mM) | 15% | 85% | ≦15 min |
| 5% (680 mM) | | 100% | ≦15 min |

EXAMPLE 2

The same procedure as in Example 1 was followed, except that ethanol, and isomers of propanediol and butanediol were used as test compounds. The results are set forth in Tables 3 and 4. The data demonstrate that several isomers of propanediol and butanediol induce melanogenesis and differentiation of S91 melanoma cells. Both 50 mM propanediol (PG) or butanediol (BD) resulted in an approximate 1.5-fold increase of melanogenesis, while 150 mM resulted in about a 2-fold increase following a single treatment. Whereas 1,2 propanediol (PG-1,2) and (S)-(+)-1,2-Propanediol (PG-S-1,2) resulted in no reduction of cell proliferation at the levels used in this experiment, 150 mM 1,3-propanediol (PG-1,3), 2,3-butanediol (BD-2,3) or 1,3-butanediol (BD-1,3) resulted in a reduction of cell numbers by one-third. In addition, the butanediols appeared to result in greater differentiation of S91 cells than the propanediols, as evidenced by earlier and greater morphological changes, and in the case of BD-2,3, a more adherent phenotype. Ethanol (EtOH) had no effect on cells at 340 mM but was toxic at 850 mM as indicated by low cell survival. Ethanol did not induce melanogenesis at any iconcentration tested. Glycerol (G) had only a slight effectton melanogenesis and differentiation at the concentrations tested in this experiment, indicating that triols may be less effective inducers of these phenotypes than diols.

TABLE 3

| | Cells (×10$^6$) | ug Melanin | pg Melanin/Cell |
|---|---|---|---|
| Control | 0.100 | 1.17 | 11.7 |
| 1.0% ETOH[1] | 0.104 | 1.14 | 11.0 |

TABLE 3-continued

|  | Cells (x10⁶) | ug Melanin | pg Melanin/Cell |
|---|---|---|---|
| 2.0% ETOH[2] | 0.100 | 1.25 | 12.5 |
| 5.0% ETOH[3] | 0.032 | 0.17 | 5.3 |
| 50 mM PG-1,2 | 0.084 | 1.31 | 15.6 |
| 150 mM PG-1,2 | 0.072 | 1.73 | 24.0 |
| 50 mM PG-S-1,2 | 0.088 | 1.51 | 17.1 |
| 150 mM PG-S-1,2 | 0.080 | 2.04 | 25.5 |
| 50 mM PG-1,3 | 0.064 | 1.31 | 20.4 |
| 150 mM PG-1,3 | 0.044 | 1.04 | 23.6 |
| 50 mM G | 0.092 | 1.03 | 11.2 |
| 150 mM G | 0.084 | 1.09 | 13.0 |
| 50 mM BD-2,3 | 0.072 | 1.12 | 15.6 |
| 150 mM BD-2,3 | 0.040 | 0.95 | 23.3 |
| 50 mM BD-1,3 | 0.064 | 0.99 | 15.5 |
| 150 mM BD-1,3 | 0.048 | 0.87 | 18.1 |

[1]170 mM
[2]340 mM
[3]850 mM

TABLE 4

|  | Morphology | | Trypsinization Detachment Time |
|---|---|---|---|
|  | Rounded Spindly | Flattened Cuboidal |  |
| Control | 100% |  | 3 min |
| 1.0% ETOH | 100% |  | 3 min |
| 2.0% ETOH | 100% |  | 3 min |
| 5.0% ETOH | 100% |  | 3 min |
| 50 mM PG-1,2 | 75% | 25% | 3 min |
| 150 mM PG-1,2 | 50% | 50% | 6 min |
| 50 mM PG-S-1,2 | 75% | 25% | 3 min |
| 150 mM PG-S-1,2 | 50% | 50% | 6 min |
| 50 mM PG-1,3 | 75% | 25% | 3 min |
| 150 mM PG-1,3 | 50% | 50% | 6 min |
| 50 mM G | 100% |  | 3 min |
| 150 mM G | 75% | 25% | 3 min |
| 50 mM BD-2,3 | 25% | 75% | 3 min |
| 150 mM BD-2,3 |  | 100% | 9 min |
| 50 mM BD-1,3 | 25% | 75% | 3 min |
| 150 mM BD-1,3 |  | 100% | 6 min |

Melanogenesis is the most characteristic feature of melanocyte differentiation (*J. Cell Sci.* 107:1095–1103, 1994), and, is inversely correlated with rate of proliferation in melanoma cell lines (*Neoplasia* 31:545–9, 1984; *Biochem. Biophys. Res. Commun.* 177:545–50, 1991; *Exp. Dermatol.* 4:192–198, 1995). As a general rule, increased proliferation commensurate with dedifferentiation are hallmarks of rapid tumor progression and a poor prognosis, while decreased proliferation and differentiation are indicative of more long-term survival (*Introduction to the Cellular and Molecular Biology of Cancer*, L. M. Franks and N. Teich, 1987, Oxford University Press). Thus, the ability of the present compounds to induce melanogenesis and slow cell growth is indicative of their ability to act as chemotherapeutic agents. Induction of melanogenesis combined with a reduced rate of cellular proliferation is indicative of induction of differentiation in S91 cells. In addition, the change of cellular morphology from a rounded, spindly appearance to a flattened, cuboidal appearance is further indication of differentiation in S91 cells (*Exp. Cell Res.* 191:209–218, 1990). Thus, the compounds of the present invention are not only tanning agents, but also chemotherapeutic agents capable of delaying tumor progression and increasing long-term survival.

It should be noted that the effects of propylene glycol (Example 1) and related diols and triols (Examples 1 & 2) on S91 cells are identical to those resulting from treatment of S91 cells with retinoids; that is, induction of melanogenesis, induction of differentiation, increased adherence, and inhibition of proliferation (Laukharanta, et al., *Arch. Dermatol. Res.* 277:147–150, 1985). Given this similarity of biological responses, it is believed that the agents described herein are effective in treating those disorders presently treated with the retinoids including a variety of forms such as psoriasis, acne and dermatoses.

EXAMPLE 3

The same procedures as in Examples 1 and 2 were followed to examine the effect of additional compounds on melanogenesis in S91 cells. The results described in Table 5 show the concentration of a number of compounds required to induce 2-fold or greater melanization in S91 cells. Many compounds are more potent than those described in Examples 1 and 2. For example, 2,3-pyridinediol was potent at 100 uM; 1,4-dioxane-2,3-diol and β-estradiol at 500 uM; 5-norbornene-2,2-dimethanol at 5 mM; 3,3-dimethyl-1,2-butanediol and 1,2-cis-cyclopentanediol at 10 mM; and 2,3-dimethyl-2,3-butanediol at 25 mM. All of the compounds listed in Table 5 except 1,4-dioxane-2,3-diol, induced transformation of S91 cells from a rounded bipolar morphology to a flattened cuboidal multipolar morphology concomitant with induction of melanogenesis; this indicates their potential usefulness as chemotherapeutic agents that act by inducing differentiation of tumor cells. All of the compounds listed in Table 5 except 5-norbornene-2,2-dimethanol, β-estradiol, and 2,3-pyridinediol induced increased trypsinization time concomitant with induction of melanogenesis; alterations of adherence properties are related to changes of metastatic potential of tumor cells.

TABLE 5

| Compound | Concentration Required for ≧2-fold Melanin Induction in S91 Cells |
|---|---|
| 2,3-Pyridinediol | 100 uM |
| 1,4-Dioxane-2,3-Diol | 500 uM |
| β-Estradiol | 500 uM |
| 5-Norbornene-2,2-Dimethanol | 5 mM |
| 1,2-cis-Cyclopentanediol | 10 mM |
| 3,3-Dimethyl-1,2-Butanediol | 10 mM |
| 2,3-Dimethyl-2,3-Butanediol | 25 mM |
| 1,2-trans-Cyclopentanediol | 50 mM |
| 2-Methyl-1,3-Propanediol | 50 mM |
| 2,3-Butanediol | 100 mM |
| 1,2-Propanediol | 150 mM |

Compounds in addition to those described in Examples 1 and 2, that did not induce significant (22-fold increase) melanogenesis in S91 cells when tested over a range of concentrations up to a toxic dose included: 1-propanol; 2-propanol; oleic acid; 2-phenyl-1,2-propanediol; 1,3-cyclohexanediol; tartaric acid; ascorbic acid; Azone®, 2-pyrrolidone; D-ribose; 2-deoxy-D-ribose; N-methyl-D-glucamine; hydroxymethyl uracil; and tetrabutylammonium chloride. Of these compounds, only 2-pyrrolidone resulted in profound morphological differentiation of S91 cells, indicating that it may augment melanogenesis and/or exert antitumorigenic activity in the absence of melanogenesis.

The PKC inhibitors H7 (1-[5-isoquinolinyl-sulfonyl]-2-methyl-piperazine) and D-sphingosine also induced melanogenesis in S91 cells. In addition, these PKC inhibitors enhanced melanogenesis induced by propylene glycol in S91 cells. These results indicate that propylene glycol does not induce melanogenesis by induction of PKC, or require PKC for induction of melanogenesis.

EXAMPLE 4

Normal human epidermal melanocytes (NHEMs) were examined for induction of melanogenesis using cells and media from Clonetics Corporation (San Diego, Calif.). Cells were cultured exactly as specified by the supplier. Based on induction of a 1.5-fold increase of melanin in NHEMs, the most potent compound examined was 2,3-pyridine-diol at 200 uM, followed by 5-norbornene-2,2-dimethanol at $\leq 5$ mM, 3,3-dimethyl-1,2-butanediol at 12.5 mM, and 2,3-dimethyl-2,3-butanediol and 1,2-cis-cyclopentanediol at 50 mM (Table 6). D-Ribose was inactive in NHEMs when tested over a range of concentrations up to a toxic dose. These results show that compounds of the present invention that exhibit activity in S91 cells, also exhibit activity in normal human melanocytes.

TABLE 6

| Compound | Concentration Required for $\geq$1.5-fold Melanin Induction in NHEMs |
| --- | --- |
| 2,3-Pyridinediol | 200 uM |
| 5-Norbornene-2,2-Dimethanol | 5 mM |
| 3,3-Dimethyl-1,2-Butanediol | 12.5 mM |
| 1,2-cis-Cyclopentanediol | 50 mM |
| 2,3-Dimethyl-2,3-Butanediol | 50 mM |
| 1,2-Propanediol | 150 mM |

EXAMPLE 5

Compounds were tested for melanogenic activity in vivo by application to American short-haired guinea pigs. Treatment sites were created by removal of fur using Nair® brand depilatory. Compounds were applied in 25 Al volumes twice per day for 5 days to each treatment spot as indicated in Table 7. In the Table, the numbers presented are the relative melanogenesis rating (mean±SE), and are arranged according to the relative location on the animal, with the head being to the left and the tail being to the right. Propylene glycol (PG=13.6M), 2,3-butanediol (2,3-BD=10.95M), and 1,2-cis-cyclopentanediol (1,2-cs-CPD=10.7M) were applied as full strength solutions. 3,3-dimethyl-1,2-butanediol (3,3-M-1,2-BD) was applied as a 4M solution dissolved in ethanol. Two weeks following cessation of treatments, the degree of pigmentation was subjectively rated according to the following scale:

| 0 | no change |
| --- | --- |
| 0.5 | slight darkening, not easily discernible |
| 1 | slight darkening, easily discernible |
| 2 | moderate, even darkening |
| 3 | substantial, even darkening |
| 4 | profound, even darkening |

The results presented below showed that there was a progressive diminution of response to tanning agents from head to tails of animals. The magnitude of this diminished response was 3- to 4-fold. Thus, comparisons between treatment compounds were done relative to similar locations on the body of guinea pigs. Propylene glycol resulted in significant melanogenesis relative to depilatory treated controls located at the same relative body position. 2-methyl-1,3-propylene glycol and 2,3-butanediol were only slightly better melanogenic agents than propylene glycol. However, 3,3-dimethyl-1,2-butanediol and 1,2-cis-cyclo-pentanediol resulted in 4.5-fold and 5.5-fold greater melanogenesis than PG applied at similar body locations.

TABLE 7

| | Treatment Head <----------------------------------------> Tail | | | |
| --- | --- | --- | --- | --- |
| | a | b | c | d |
| PG, 5 Days (n = 6): | | | | |
| | 1.04 ± 0.21 | 0.83 ± 0.17 | 0.25 ± 0.09[1] | 0.33 ± 0.16[1] |
| 5 days (n = 3): | | | | |
| | 2-M-PG | 2,3-BD | 2-M-PG | 2,3-BD |
| | 1.25 ± 0.52 | 1.33 ± 0.17[2] | 0.58 ± 0.082 | 0.25 ± 0.14 |
| 5 Days (n = 3): | | | | |
| | Nair | PG | 3.3-M-1.2-BD | 1.2-cs-CPD |
| | 0[2] | 0.50 ± 0.25 | 1.16 ± 0.66[2] | 1.83 ± 0.33[2] |

Figure 1C:
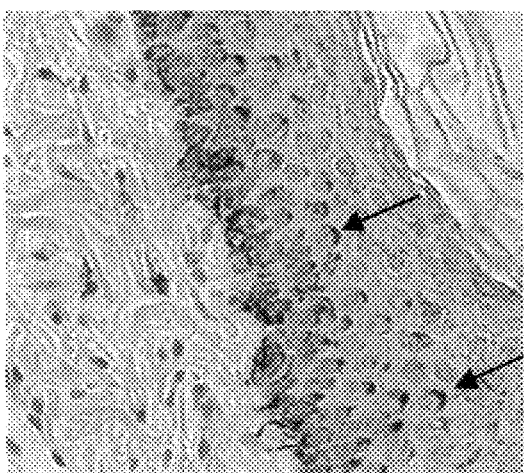
Figure 1D:
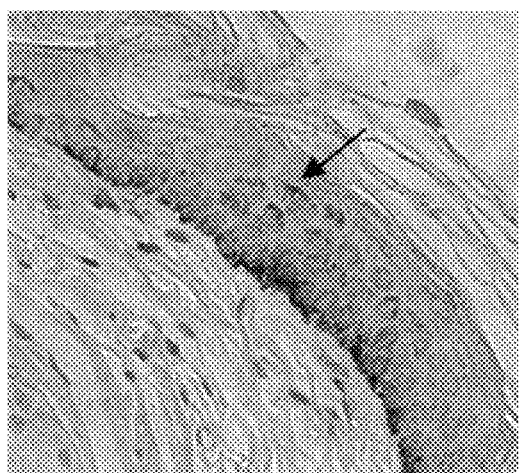

[1] $P < 0.05$ relative to PG-treated site located nearest head in first row
[2] $P < 0.05$ relative to PG-treated site in first row that is located at same position relative to head and tail In order to minimize the effects of diminution of response from head to tails of animals, all future experiments were done using only treatment spots located towards the tails of animals (c and d in Table 7). Deemed as additionally beneficial, in this area of the animal differences of responsiveness to strong and weak inducers of pigmentation, as deduced from cell culture, were greatest. Comparison of the pigmentation ratings of these treatment spots showed the following descending order of induction: 8.7M 1,2-cis-cyclopentanediol (1,2-cs-CPD)>4M 3,3-di-methyl-1,2-butanediol (3,3-M-1,2-BD)>a mixture of 8.5M 1,2-propylene glycol (1,2-PG)/1M 5-norbornene-2,2-dimethanol (5-NBene-2,2-DM)/2% 2-pyrrolidone (2-P; a penetration enhancer)>1M 5-NBene-2,2-DM/2% 2P, >11.3M 2-methyl-1,3-propylene glycol (2-M-1,2-PG) (Table 8; FIG. 1A: untreated; 1B: 10.6M 1,2-PG/2% 2-P; 1C: 8.7M 1,2-cs-CPD; 1D: 1M 5NBene-2,2-DM/8.5M 1,2-PG/2% 2-P). In this region of the animals, responses to 13.61M 1,2-PG; 10.6M 1,2-PG/2% 2P, and 11M 2,3-dimethyl-2,3-butanediol were not significantly different from control (Nair or 2% 2P treated) spots. Pigmentation ratings were corrected for background (control treatment spots), normalized to 1M to account for the different amounts of each agent applied, and then normalized to results for 1,2-PG (Table 8). This comparison showed that the descending order of induction was 5-NBene-2,2-DM>1,2-cs-CPD>2-M-1,3-PG, and, that using 1,2-PG as carrier for 5-NBene-2,2-DM (FIG. 1D) increased responsiveness to this compound. It is anticipated that further improvements in formulation will additionally improve responsiveness to 5-NBene-2,2-DM and other compounds in this invention. Biopsies results (FIG. 1) showed that induction of melanogenesis was marked by deposition of melanin in keratinocytes, in some cases with formation of "supranuclear caps" (arrows, FIG. 1C & 1D) indicative of induction of true natural UV-protective melanogenesis (Gates, R. R., and A. A. Zimmermann, 1953 *J. Invest. Dermatol.* 21:339–348), and a complete absence of inflammation, fibrosis or any other form of tissue damage.

TABLE 8

| Treatment | Pigmentation Ratina | Background Corrected | Normalized to 1 M | Normalized to 1,2-PG |
|---|---|---|---|---|
| No Penetration Enhancer | | | | |
| Nair | 0.08 ± 0.05 (n = 6) | 0 | | |
| 13.61 M 1,2-PG | 0.29 ± 0.09 (n = 12) | 0.21 ± 0.03 | 0.015 ± 0.002 | 1.0 ± 0.1 |
| 11.0 M 2,3-M-2,3-BD | 0.25 ± 0.14 (n = 3) | 0.17 ± 0.09 | 0.015 ± 0.008 | 1.0 ± 0.6 |
| 11.3 M 2-M-1,3-PG | 0.58 ± 0.08* (n = 3) | 0.50 ± 0.07 | 0.044 ± 0.006 | 2.9 ± 0.4 |
| 8.7 M 1,2-cs-CPD | 1.89 ± 0.27* (n = 9) | 1.75 ± 0.25 | 0.202 ± 0.029 | 13.5 ± 1.9 |
| 4.0 M 3,3-M-1,2-BD | 1.17 ± 0.44* (n = 3) | 1.09 ± 0.41 | 0.272 ± 0.102 | 18.1 ± 6.8 |
| Penetration Enhancer 2% 2-Pyrrolidone | | | | |
| 2P | 0.17 ± 0.08 (n = 6) | 0 | | |
| 10.6 M 1,2-PG/2P | 0.33 ± 0.05 (n = 6) | 0.16 ± 0.02 | 0.015 ± 0.002 | 1.0 ± 0.15 |
| 1.0 M 5-NBene-2,2-DM/2P | 0.66 ± 0.05* (n = 6) | 0.49 ± 0.04 | 0.490 ± 0.037 | 32.7 ± 2.5 |
| 8.5 M 1,2-PG/2P11.GM 5-NBene-2,2-DM | 1.00 ± 0.13* (n = 6) | 0.83 ± 0.11 | 0.670 ± 0.087[1] | 44.7 ± 5.8 |

*P < 0.05; Students T-test
[1]Further background corrected for pigmentation induced by 1,2-PG/2P (0.16)

EXAMPLE 6

Compounds were examined for their ability to induce tyrosinase activity in S91 mouse melanoma cells. Tyrosinase is the rate limiting enzyme in the melanogenic pathway. Its measurement provides a highly specific and sensitive indication of degree of induction of melanogenesis by test compounds. All cell culture conditions and treatments were as described above in Examples 1–3. Following treatments, cells were trypsinized, counted by Coulter, pelleted by centrifugation at 1000×g, and analyzed for tyrosinase activity using modifications of previously described procedures (Pomerantz, S. H., 1966, *J. Biol. Chem.* 241:161–168; Jara, et al., 1988, *Pigment Cell Res.* 1:332–339.). Briefly, cell pellets were solubilized by sonicating for 5 seconds in 600 ul 50 mM phosphate buffer pH 6.8 containing 0.5% Triton-X100, followed by vortexing, incubation on ice for 30 min, and then revortexing. From this, 200 ul aliquots were combined with 200 ul of reaction mixture containing either 75 uM tyrosine, 75 uM L-Dopa, and 2 uCi L-[3,5-$^3$H] Tyrosine in 50 mM NaPO$_4$ pH 6.8 (L-Dopa +), or, 75 uM tyrosine, and 2 uCi L-[3,5-$^3$H]Tyrosine in 50 mM NaPO$_4$ pH 6.8 (L-Dopa −) and incubated 1 hr at 37° C. Reactions were stopped by addition of 400 ul 10% activated charcoal in 0.1N HCl and incubation on ice for 15 min. This mixture was centrifuged at 17,300×g for 5 min, and 400 ul supernatant was then filtered through a 0.22 uM GV Durapore centifugal filter unit (Millipore) by centrifuging at 17,300×g for 5 min. Filtrate was added to 4 ml Fisher Plus scintillation fluid and counted on a Hewlett Packard scintillation counter. Tyrosinase activity was calculated as dpm/hr/ug protein and dpm/hr/10$^3$ cells. Each sample was analyzed with and without L-Dopa, a necessary cofactor for tyrosinase (Pomerantz, S. H., 1966, *J. Biol. Chem.* 241:161–168; McLane, et al., 1987, *Biochem. Biophys. Res. Commun.* 145:719–725). All reported tyrosinase values are exclusive of counts that occurred in buffer blanks and L-dopa negative aliquots. Protein was determined on aliquots of cell lysate, extracellular particulate lysate or media by the Bradford Coomassie Blue method (Bradford, 1967, *Anal. Biochem.* 72:248–254) using Bio-Rad Protein Assay Kit I.

Results (Table 9; mean±SE) show that 3,3-dimethyl-1,2-butanediol (3,3-M-1,2-BD) and 5-norbornene-2,2-dimethanol (5-NBene-2,2-DM) result in the greatest induction of tyrosinase on both a cellular and protein basis. Although 100 uM 2,3-pyridinediol (2,3-Pyd) induced 2-fold increases of melanin (Example 3, Table 5), even 500 uM 2,3-Pyd induced only low levels of tyrosinase relative to that induced by 5 mM 5-NBene-2,2-DM or 3,3-M-1,2-BD, and, higher levels of 2,3-Pyd were toxic. 5-NBene-2,2-DM and 3,3-M-1,2-BD are nontoxic at concentrations that induce much higher levels of tyrosinase, and thus are preferred agents for induction of melanogenesis in this embodiment. Since 5-NBene-2,2-DM induces nearly equivalent levels of tyrosinase at 5-fold lower concentrations than 3,3-M-1,2-BD, it is particularly preferred. IBMX (3-isobutyl-1-methylxanthine) is well known to those in the art as potent inducer of melanogenesis and tyrosinase, and is provided as a positive control.

TABLE 9

| Sample #/Treatment | dpm/hr 10$^3$ Cells | dpm/hr ug Protein |
|---|---|---|
| Control (n = 4) | 40 ± 6 | 184 ± 27 |
| 300 mM PG-1,2 (n = 4) | 292 ± 104 | 1003 ± 370 |
| 25 mM 3,3-M-1,2-BD (n = 2) | 1211 ± 38 | 1746 ± 220 |
| 50 mM 1,2-cs-CPD (n = 2) | 276 ± 16 | 925 ± 53 |
| 5 mM 5-NBene-2,2-DM (n = 4) | 707 ± 54 | 1643 ± 105 |
| 0.5 mM 2,3-Pyd (n = 2) | 142 ± 8 | 160 ± 19 |
| 0.1 mM IBMX (n = 2) | 765 ± 53 | 2161 ± 41 |

Figure 2:
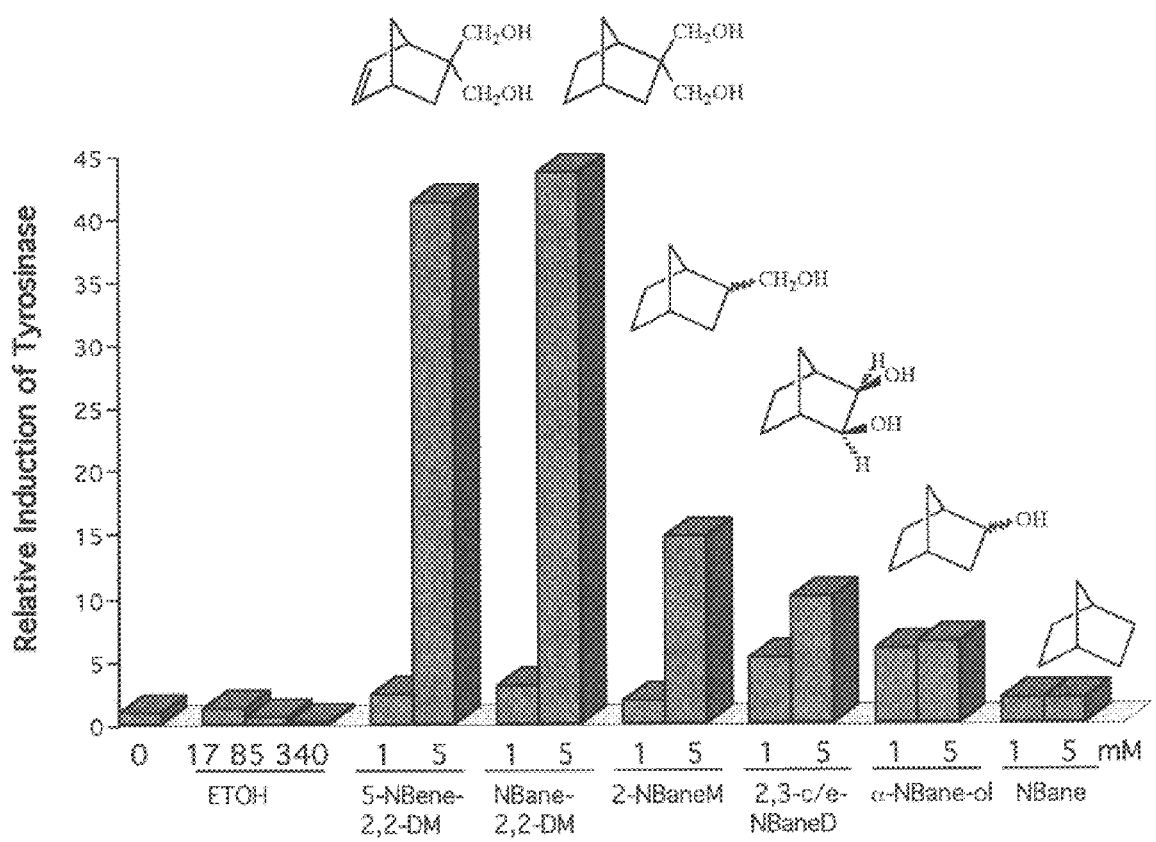
FIG. 2 is a series of bar graphs depicting the structure activity results obtained in Example 7.

Structure activity studies with 5-NBene-2,2-DM and related compounds indicate that norbornane-2,2-dimethanol (NBane-2,2-DM) has equivalent potency for induction of tyrosinase in S91 cells (FIG. 2). Thus, NBane-2,2-DM is equivalently preferred with 5-NBene-2,2-DM. Lesser induction of tyrosinase in S91 cells was induced in descending order by 2-Norbornanemethanol (2-NBaneM), 2,3-cis/exo-Norbornanediol (2,3-c/e-NBaneD), α-Norborneol (α-NBane-ol), and Norbornane (NBane). Since even NBane results in 2-fold induction of tyrosinase relative to untreated or ethanol (ETOH) treated control S91 cells, it is included as a component of this invention. In addition, since NBane induces melanogenesis, it is contemplated that all compounds containing NBane as a component of their structure may induce melanogenesis. In addition, compounds containing Norbornene (NBene) or any other unsaturated compound derived form norbornane are expected to induce melanogenesis. Thus, any saturated or unsaturated compound derived from or related to norbornane is included as a component of this invention, including but not limited to compounds derived from bornane, pinane, camphene and camphor.

Neither the highly specific protein kinase A (PKA) inhibitor H-89 (N-[2-(p-bromocinnamylamino)-ethyl]-5-isoquinolinesulfinamide.2HCl; Chijiwa, et al., 1990, *J. Biol. Chem.* 265:5267–5272), nor the highly specific protein kinase C (PKC) inhibitor GF109203X (Bisindolylmaleimide; Toullec, et al., 1991, *J. Biol. Chem.* 266:15771–15781) inhibited induction of tyrosinase by 5-NBene-2,2-DM (Table 10). Thus, similar to results described for 1,2-propanediol in Example 3, 5-NBene-2,2-

DM and related compounds are unlikely to act via activation of PKC pathways, which have been described as important for induction of melanogenesis by diacylgerols (Allan, et al., 1995, *J. Invest. Dermatol.* 105:687–692; Gilchrest, et al., 1996, *Photochem. Photobiol.* 63:1–10). Nor are 5-NBene-2,2-DM or related compounds likely to act via activation of PKA pathways, described as important for induction of melanogenesis by IBMX (Fuller, et al., 1993, *Ann. NY Acad. Sci.* 690:302–319; Fuller, et al., 1996, *Pigment Cell Res.* S5:65). Furthermore, addition of catalase to the cell culture media did not inhibit the action of 5-NBene-2,2-DM, indicating that unlike L-Dopa and Dopac, this and related compounds are unlikely to induce melanogenesis via generation of hydrogen peroxide or other reactive oxygen species (Karg, et al., 1989, *Acta Derm. Venereol.* 69:521–524; Karg, et al., 1991. *J. Invest. Dermatol.* 96:224–227; Karg, et al., 1993, *J. Invest. Dermatol.* 100:209S–213S).

TABLe 10

|  | Tyrosinase dpm/hr/ ug Protein | Relative to Control |
| --- | --- | --- |
| Control | 398 | 1 |
| 5 mM 5-NBene-2,2-DM | 3273 | 8.2 X |
| 1 uM H-89 | 507 | 1.3 X |
| 10 uM H-89 | 1236 | 3.1 X |
| 1 uM H-89/ 5 mM 5-NBene-2,2-DM | 4624 | 11.6 X |
| 10 uM H-89/ 5 mM 5-NBene-2,2-DM | 3093 | 7.8 X |
| 0.1 uM GF109203X | 1025 | 2.6 X |
| 1 uM GF109203X | 2407 | 6.1 X |
| 0.1 uM GF109203X/ 5 mM 5-NBene-2,2-DM | 4679 | 11.8 X |
| 1 uM GF109203X/ 5 mM 5-NBene-2,2-DM | 6531 | 16.4 X |
| 500 Units Catalase/ml | 745 | 1.9 X |
| 1000 Units Catalase/ml | 691 | 1.7 X |
| 500 Units Catalase/ml/ 5 mM 5-NBene-2,2-DM | 2796 | 7.0 X |
| 1000 Units Catalase/ml/ 5 mM /5-NBene-2,2-DM | 4778 | 12.0 X |

Example 7

Tyrosinase was measured in normal human epidermal melanocytes (NHEM) using procedures identical to those described for S91 cells (Example 6), except that media from 5 day treatment periods was retained and centrifuged at 200×g, 1600×g, or 17,300×g for analysis of tyrosinase activity in the extracellular exported melanosomal particulate fraction, and in the resultant supernatant media fraction. In some cases (Table 11), tyrosinase was also measured by an in situ assay wherein radiolabelled tyrosine was added directly to freshly replaced media of NHEM for a period of 24 hrs following a 5 day treatment period (Abdel-Malek, et al., 1992, *J. Cell. Physiol.* 150:416–425). Results showed that 5 mM 5-NBene-2,2-DM induced tyrosinase to a greater extent in the in situ assay, in cells, in extracellular particulate melanosomal fractions, and in the media of NHEM than did 25 mM 3,3-M-1,2-BD (Table 11). Both 5 mM 5-NBene-2, 2-DM and 25 mM 3,3-M-1,2-BD induced more tyrosinase in each of these assays and fractions than did 1,2-PG. IBMx (3-isobutyl-1-methyl-xanthine) provided as a positive control, induced as much tyrosinase as 5 mM 5-NBene-2, 2-DM in the in situ assay, but less in cellular, extracellular particulate and media fractions (Table 11).

TABLE 11

| | Tyrosinase dpm/hr/$10^3$ Cells | | | | |
| --- | --- | --- | --- | --- | --- |
| | In Situ | Cellular | 200 g Partic | 17300 g* Partic | Media** |
| Control | 16.8 | 10259 | 244 | 97 | 1457 |
| 85 mM ETOH | 15.0 (1.00 X) | 10201 (1.00 X) | 442 (1.00 X) | 132 (1.00 X) | 1654 (1.00 X) |
| 300 mM 1,2-PG | 16.8 | 10247 | 433 | 102 | 1864 |
| 300 mM 1,2-PG | 17.2 (1.07 X) | 10875 (1.03) | 923 (1.98 X) | 241 (1.50 X) | 2123 (1.28 X) |
| 25 mM 3,3-M-1,2-BD | 20.5 | 11728 | 1646 | 536 | 5495 |
| 25 mM 3,3-M-1,2-BD | 21.0 (1.31 X) | 11730 (1.15 X) | 2226 (5.64 X) | 425 (4.20 X) | 3056 (2.75 X) |
| 5 mM 5-NBene-2,2-DM | 24.5 | 13838 | 6447 | 493 | 4164 |
| 5 mM 5-NBene-2,2-DM | 25.4 (1.57 X) | 14716 (1.40 X) | 6291 (18.6 X) | 473 (4.22 X) | 4639 (2.83 X) |
| 0.1 mM IBMX | 25.3 | 10910 | 2189 | 220 | 2698 |
| 0.1 mM IBMX | 26.1 (1.62 X) | 11737 (1.11 X) | 1834 (5.86 X) | 260 (2.10 X) | 2935 (1.81 X) |

*Post 200 × g
**Post 17300 × g

Further studies using NHEM demonstrated that, similar to results for S91 cells (FIG. 2), compounds related to 5-NBene-2,2-DM may be inducers of tyrosinase (Table 12). For example, 2-norbornanemethanol (2-NBaneM) resulted in induction of tyrosinase at levels equivalent to 5-NBene-2,2-DM in NHEM both from a white adult donor and a black neonatal donor (Table 12). Thus, similar to S91 cells (Example 6), all norbornane-related compounds are contemplated to induce tyrosinase in NHEM and are thereby embodied in this invention.

TABLE 12

| | White-Adult-NHEM Tyrosinase dpm/hr/$10^3$ cells | | |
| --- | --- | --- | --- |
| | In Situ | Cellular | Media[1] |
| Control | 5.56 (1.00 X) | 13992 (1.00 X) | 36.3 (1.00 X) |
| 1 mM 5-NBene-2,2-DM | 6.27 (1.13 X) | 12740 (0.91 X) | 29.9 (0.82 X) |
| 5 mM 5-NBene-2,2-DM | 5.81 (1.04 X) | 18467 (1.32 X) | 53.1 (1.46 X) |
| 1 mM 2-NBaneM | 7.05 (1.27 X) | 15257 (1.09 X) | 29.2 (1.11 X) |
| 5 mM 2-NBaneM | 6.18 (1.11 X) | 16077 (1.15 X) | 48.1 (1.33 X) |

| | Black-Neonatal-NHEM dpm/hr/$10^3$ cells | | |
| --- | --- | --- | --- |
| | In Situ | Cellular | Media |
| Control | 12.5 (1.00 X) | 9856 (1.00 X) | 11.1 (1.00 X) |
| 1 mM 5-NBene-2,2-DM | 13.9 (1.11 X) | 10679 (1.08 X) | 26.8 (2.41 X) |
| 5 mM 5-NBene-2,2-DM | 14.1 (1.13 X) | 15398 (1.56 X) | 33.2 (2.99 X) |
| 1 mM 2-NBaneM | 12.1 (0.97 X) | 10863 (1.10 X) | 18.7 (1.68 X) |
| 5 mM 2-NBaneM | 12.8 (1.02 X) | 17397 (1.77 X) | 37.3 (3.36 X) |

[1]Unlike Table 11 where Media was from a 5 day treatment period, Media in Table 12 was from a 1 day treatment period.

Example 8

Figure 3A:
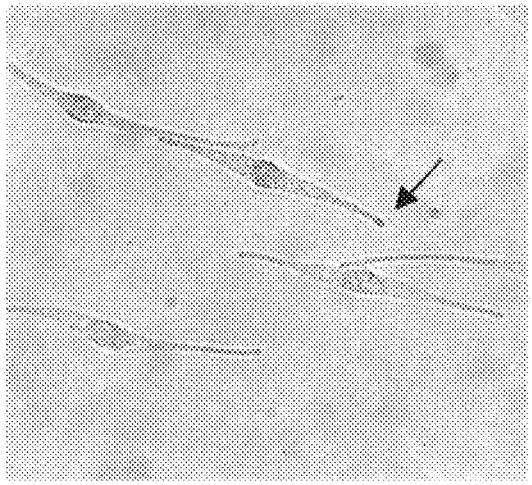
FIGS. 3A–3D are printouts of normal human epidermal melanocytes and melanosomes as described in Example 8.
Figure 3B:
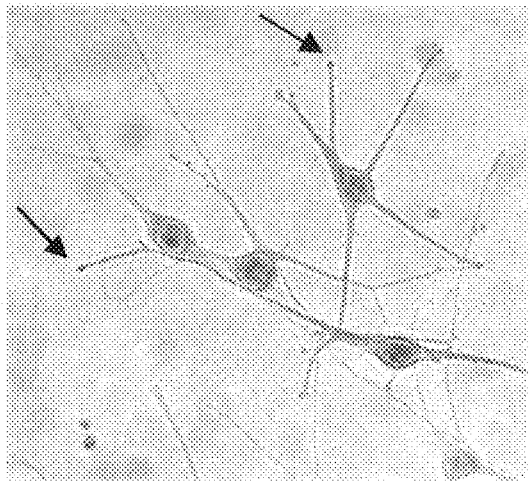
Figure 3C:
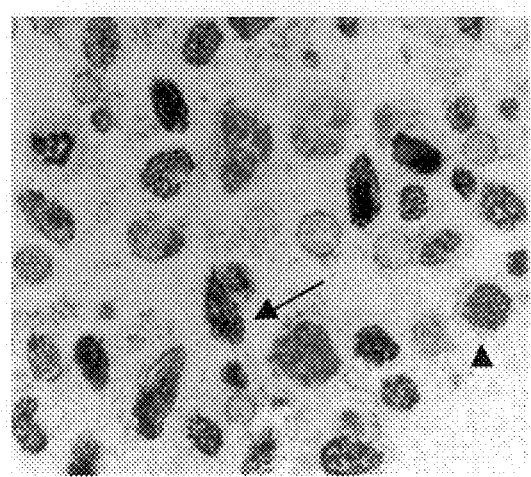
Figure 3D:
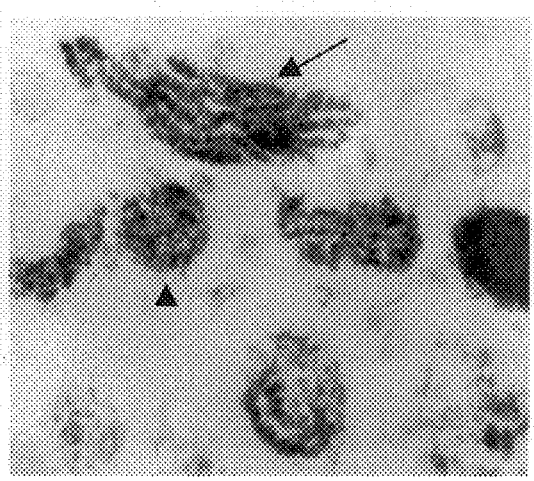

Similar to results for S91 cells treated with diols (Examples 1 and 2), treatment of normal human epidermal melanocytes (NHEM) with 5 mM 5-NBene-2,2-DM resulted in morphological changes indicative of differentiation. In the case of NHEM, induction of differentiation was marked by conversion of cells from a bipolar phenotype to a multidendritic phenotype (compare untreated NHEM in FIG. 3A with 5mM 5-NBene-2,2-DM treated NHEM in FIG. 3B). Additionally, the length of dendrites was increased approximately 2-3-fold following treatment with 5 mM 5-NBene-2,2-DM, and there was an increase in the number of secretory vesicles at the termini of dendrites (arrows in FIGS. 3A and 3B). Electron microscopic analysis indicated that the extracellular particulate fraction secreted into the media from NHEM was comprised almost exclusively of stage III and IV melanosomes (arrows show longitudinal view and arrowheads show cross-sectional view in FIGS. 3C and 3D). Increased secretion of melanosomes resulting from treatment with 5 mM 5-NBene-2,2-DM was reflected in increased extracellular particulate tyrosinase activity (Example 7, Table 11).

It is well known that ultraviolet irradiation of skin results in increased dendricity of melanocytes and increased transport of melanosomes from the ends of dendritic processes to neighboring kerat,nocytes (Jimbow, et al., *Biology of Melanocytes*, pp. 261–289, In: Dermatology in General Medicine, eds: Fitzpatrick, et al., McGraw-Hill, 1994). Thus, secretion of melanosomes from melanocytes treated with 5-NBene-2,2-DM appears to parallel the physiological processes induced by sunlight in skin.

EXAMPLE 9

Highly specific inhibitors of the cAMP/PKA (protein kinase A) or PKC (protein kinase C) pathways do not inhibit induction of melanogenesis by 5-NBene-2,2-DM in S91 cells (Example 6, Table 10). However, each of the nitric oxide (NO) scavenger PTIO (2-phenyl-4,4,5,5-tetramethyl-imidazoline-1-oxyl-3-oxide), the cyclic guanosine monophosphate (cGMP) inhibitor LY83583 (6-anilino-5,8-quinolinequinone), and the PKG (protein kinase G) inhibitor KT58223 reduce induction of melanogenesis by 5-NBene-2,2-DM in S91 cells (Table 13). These results demonstrate that induction of melanogenesis by 5-NBene-2,2-DM occurs by the NO/cGMP/PKG pathway. Furthermore, results are similar to those obtained for ultraviolet radiation wherein induction of melanogenesis did not occur via either the cAMP/PKA or PKC pathways (Friedmann and Gilchrest, 1987, *J. Cell. Physiol* 133:88–94; Carsberg, et al., *J. Cell. Sci.* 107:2591–2597), but rather occurred via the NO/cGMP/PKG pathway (Romero-Graillet, et al., 1996, *J. Biol. Chem.* 271:28052–28056; Romero-Graillet, et al., 1997, *J. Clin. Invest.* 99:635–642). Moreover, unlike IBMX (3-isobutyl-1-methylxanthine) and MSH (melanocyte stimulating hormone) which induce melanogenesis by the cAMP/PKA pathway (Wintzen and Gilchrest, 1996, *J. Invest. Dermatol.* 106:3–10; Fuller, et al., 1993, *Ann. NY Acad. Sci.* 690:302–319), and DAG (diacylglycerol) which induces melanogenesis by the PKC pathway (Allan, et al., 1995, *J. Invest. Dermatol.* 105:687–692), 5-NBene-2,2-DM induces melanogenesis by the NO/cGMP/PKG pathway similar to ultraviolet radiation.

It has been previously demonstrated that a variety of aliphatic and alicyclic diols including 5-norbornene-2,2-dimethanol (5-NBene-2,2-DM) induce melanogenesis in S91 cells (Examples 1–3). The results presented in Table 15 show that induction of tyrosinase (the rate-limiting enzyme in melanogenesis) by 5-NBene-2,2-DM is not blocked by highly specific inhibitors of the PKC and PKA pathways. In fact, treatment of S91 cells with either the highly specific PKA inhibitor H-89 (Chijiwa, et al., 1990, *J. Biol. Chem.* 265:5267–5272), or the highly specific PKC inhibitor GF109203X (Toullec, et al., 1991, *J. Biol. Chem.* 266:15771–15781) resulted in augmentation of basaland 5-NBene-2,2-DM-induced tyrosinase levels (Table 15). Thus, 5-NBene-2,2-DM does not appear to act via either the PKC or PKA pathways.

In contrast, both the nitric oxide (NO) scavenger PTIO (2-phenyl-4,4,5,5-tetramethylimidazoline-1-oxyl-3-oxide), the cyclic guanosine monophosphate (cGMP) inhibitor LY83583 (6-anilino-5,8-quinolinequinone), and the PKG (cGMP-activated protein kinase) inhibitor KT5823 reduced induction of melanogenesis by 5-NBene-2,2-DM in S91 cells (Table 16). These results demonstrate that induction of melanogenesis by 5-NBene-2,2-DM occurs by the NO/cGMP/PKG pathway.

Previously, it has been demonstrated that NO donors can stimulate melanogenesis in normal human melanocytes (Romero-Graillet, et al., 1996, *J. Biol. Chem.* 271). Results presented here demonstrate that 5-NBene-2,2-DM can stimulate melanogenesis with an efficacy equivalent or greater than that of NO donors, even though 5-NBene-2,2-DM has no ability to donate NO. Since induction of melanogenesis by 5-NBene-2,2-DM occurs by the NO/cGMP/PKG pathway, 5-NBene-2,2-DM must directly stimulate NO synthesis within cells.

These results demonstrate that stimulation of NO synthesis and the cGMP/PKG pathway by 5-NBene-2,2-DM provides an efficient alternative to stimulation of this pathway by NO donors. Thus, 5-NBene-2,2-DM and related compounds described in this invention will serve as alternative therapeutics for treatment of a variety of diseases mediated by perturbations of the NO/cGMP/PKG pathway.

TABLE 13

| Induction | dpm/hr/ $10^3$ cells | % of 5-NBene-2,2-DM |
|---|---|---|
| NO/PKG Inhibitors - Experiemnt 1 | | |
| 5 mM 5-NBene-2,2-DM (n = 4) | 5018 ± 415[1] | 100% |
| 5 mM 5-NBene-2,2-DM/ 20 UM PTIO[2] (n = 2) | 3703 ± 262 | 74% |
| 5 mM 5-NBene-2,2-DM/ 0.5 uM KT58233 (n = 2) | 1528 ± 190 | 31% |
| NO/PKG Inhibitors - Experiment 2 | | |
| 5 mM 5-NBene-2,2-DM (n = 4) | 5640 ± 323 | 100% |
| 5 mM 5-NBene-2,2-DM/ 20 uM PTIO[2] (n = 2) | 4078 ± 429 | 72% |
| 5 mM 5-NBene-2,2-DM/ 40 uM PTIO (n = 2) | 3351 ± 994 | 59% |
| 5 mM 5-NBene-2,2-DM/ 0.5 uM KT58233 (n = 2) | 2940 ± 261 | 52% |
| 5 mM 5-NBene-2,2-DM/ 1.0 uM KT5823 (n = 2) | 1688 ± 324 | 30% |
| cGMP Inhibitor - Experiment 3 | | |
| 5 mM 5-NBene-2,2-DM (n = 4) | 6388 ± 460[1] | 100% |
| 5 mM 5-NBene-2,2-DM/ 0.1 uM LY83583[4] (n = 2) | 1389 ± 64 | 22% |
| 5 mM 5-NBene-2,2-DM/ 0.2 uM LY83583 (n = 2) | 300 ± 84 | 5% |

[1] X ± SE
[2] PTIO: Nitric oxide scavenger
[3] KT5823: PKG inhibitor
[4] LY83583: inhibitor of cGMP formation.

EXAMPLE 10

Studies with the L-arginine analog S-ethylisothiourea (Garvey, et al., 1994, *J. Biol. Chem.* 269:26669–26676;

Southern, et al., 1995, *Br. J. Pharmacol.* 114:510–516), a competitive inhibitor of nitric oxide synthase at the L-arginine binding site, also support the contention that 5-norbornene-2,2-dimethanol acts via the nitric oxide pathway. Treatment with S-ethylisothiourea (S-EITU) resulted in a dose-response diminution of tyrosinase activity in S91 cells, with complete ablation of tyrosinase activity at 1000 nM S-EITU (Table 14).

TABLE 14

|  | Tyrosinase dpm/hr/10$^3$ Cells |
| --- | --- |
| Control | 47 |
| 86 mM ETOH | 46 |
| 5 mM 5-NBene-2,2-DM | 4515 |
| 5 mM 5-NBene-2,2-DM | 4247 |
| Avg. | 4381 |
| 5 mM 5-NBene-2,2-DM/50 nM S-EITU | 5186 |
| 5 mM 5-NBene-2,2-DM/100 nM S-EITU | 4646 |
| 5 mM 5-NBene-2,2-DM/250 nM S-EITU | 3758 |
| 5 mM 5-NBene-2,2-DM/500 nM S-EITU | 1055 |
| 5 mM 5-NBene-2,2-DM/750 nM S-EITU | 357 |
| 5 mM 5-NBene-2,2-DM/1000 nM S-EITU | Not Done |

Example 11

As a continuance of the structure activity studies described in Example 6 (FIG. 2), a variety of norbornane derivatives and related monocyclic or aliphatic derivatives were examined for melanogenic activity (Tables 15 and 16). Although many of these agents possessed significant melanogenic activity, only 2-hydroxy-2-norbornanemethanol and 1-(exo & endo-2-norbornyl-)-propan-1,2-diol induced levels of tyrosinase that approached the maximal levels induced by 5-norbornene-2,2-dimethanol (Table 16).

The results presented in Table 16 demonstrate that several different types of norbornane derivatives including triols, acetates, acetate esters, carboxylic acids, and formates possess melanogenic activity. As shown previously in Example 6, some of this activity is embodied within the norbornane structure itself, since 1 or 5 mM norbornane resulted in 2-fold induction of tyrosinase (FIG. 2). These results further substantiate the claims herein, that any compound derived from norbornane is expected to be a melanogenic agent, and is therefore included in this invention.

Low levels of melanogenic activity were also exhibited by monocyclic dimethanol compounds and a noncyclic dimethanol-containing compound (Table 16). These results demonstrate that dimethanol groups embody low levels of melanogenic activity, even in the absence of the bicyclic ring structure of norbornane. These results, combined with the finding that 2-norbornanemethanol exhibits significant melanogenic activity (FIG. 2; Table 12), demonstrate that any compound containing one or more methanol groups has the potential to be a melanogenic agent, and these are therefore also included in this invention.

TABLE 15

Fold Induction of Tyrosinase Relative to Controls

|  | 1 mM | 2 mM | 5 mM |
| --- | --- | --- | --- |
| 5-norbornene-2,2-dimethanol | 4.0 X | 12.9 X | 41.9 X |
| 2,5 & 6,7-norbornanetriol[1] | 5.1 X | 5.1 X | ND[2] |
| mono- & di-acetate 2,5 & 6,7-norbornanetriol | 1.5 X | 3.0 X | ND |

TABLE 15-continued

Fold Induction of Tyrosinase Relative to Controls

|  | 1 mM | 2 mM | 5 mM |
| --- | --- | --- | --- |
| 2-norbornaneacetic acid | 4.6 X | ND | 12.9 X |
| 5-norbornene-2,3-cis/endo-dicarboxylic acid | 2.2 X | ND | 1.0 X |
| ± exo-2-norbornyl formate | 2.7 X | ND | 2.3 X |

[1]5 & 6 refers to a mixture of molecular entities wherein hydroxyl substituents may be in either the 5 or 6 position
[2]ND: not done

TABLE 16

Fold Induction of Tyrosinase Relative to Controls

|  | 0.5 mM | 1 mM | 2.5 mM | 5 mM |
| --- | --- | --- | --- | --- |
| 5-norbornene-2,2-dimethanol | 2.8 X | 3.6 X | 14.5 X | 61.6 X |
| 2,7-norbornanediol | ND[1] | 0.8 X | 1.6 X | 3.5 X |
| 2-hydroxy-2-norbornane-methanol | ND | 9.2 X | 15.5 X | 45.0 X |
| 1-(exo & endo-2-norbornyl-)-propan-1,2-diol | 2.2 X | 4.2 X | 48.5 X | 2.0 X |
| methyl-5-norbornene-2,3-dimethanol | 6.0 X | 8.1 X | 0.8 X | NA[2] |
| 1,2-cis-cyclohexanedimethanol | ND | 0.9 X | 6.1 X | NA |
| 3-cyclohexane-1,1-dimethanol | ND | 1.4 X | 2.3 X | 7.0 X |
| 1,4-cyclohexanedimethanol | ND | 1.2 X | 1.7 X | 3.2 X |
| pentaerylthritol | ND | 1.2 X | 1.9 X | 1.5 X |

[1]ND: not done
[2]NA: not analyzed because cells had detached from culture dishes Example 12

Further studies using S91 cells and the methods described in Example 6 showed that 2,3-cis/exo-pinanediol ([1R,2R,3S,5R]-[−]-pinanediol) had greater melanogenic activity than 5-norbornene-2,2-dimethanol when tested over a range of concentrations (FIG. 5). 2,3-cis/exo-pinanediol induced 2.6-fold more tyrosinase activity than 5-norbornene-2,2-dimethanol when tested at 500 uM, 5.2-fold more at 1 mM, and 7.3-fold more at 2.5 mM (calculated from data in FIG. 5).

In a related experiment, nitric oxide was measured in cell-free media from S91 cells following treatment with a range of concentrations of 2,3-cis/exo-pinanediol or 5-norbornene-2,2-dimethanol for 4 days. In biological fluids, nitric oxide is converted into nitrite and nitrate with seconds of production. Therefore, nitric oxide is measured by first converting nitrate to nitrite using nitrate reductase, followed by addition of Greiss reagent to detect nitrite as optical density at 550 nm (Moshage, et al., 1995, *Clin. Chem.* 41:892–896; Schmidt, et al., 1995, *Biochemica* 2:22)). Results of this experiment showed that 2,3-cis/exo-pinanediol is a more potent inducer of nitric oxide synthesis than 5-norbornene-2,2-dimethanol (Table 17). Moreover, the relative melanogenic potency of 2,3-cis/exo-pinanediol and 5-norbornene-2,2-dimethanol shown in FIG. 5 paralleled the relative potency of these compounds with regards to induction of nitric oxide (Table 17). These results in combination with those given in Example 9 indicate that similar to induction of melanogenesis by ultraviolet irradiation (Romero-Graillet, et al., 1996, *J. Biol. Chem.* 271:28052–28056; Romero-Graillet, et al., 1997, *J. Clin. Invest.* 99:635–642), induction of melanogenesis by diols occurs via the nitric oxide pathway. It follows that measurement of induction of nitric oxide, cGMP or PKG may provide biochemically relevant screening assays for compounds that may be melanogenic. Thus, the utilization of these assays to screen compounds for melanogenic activity is claimed in the present invention.

Figure 4:
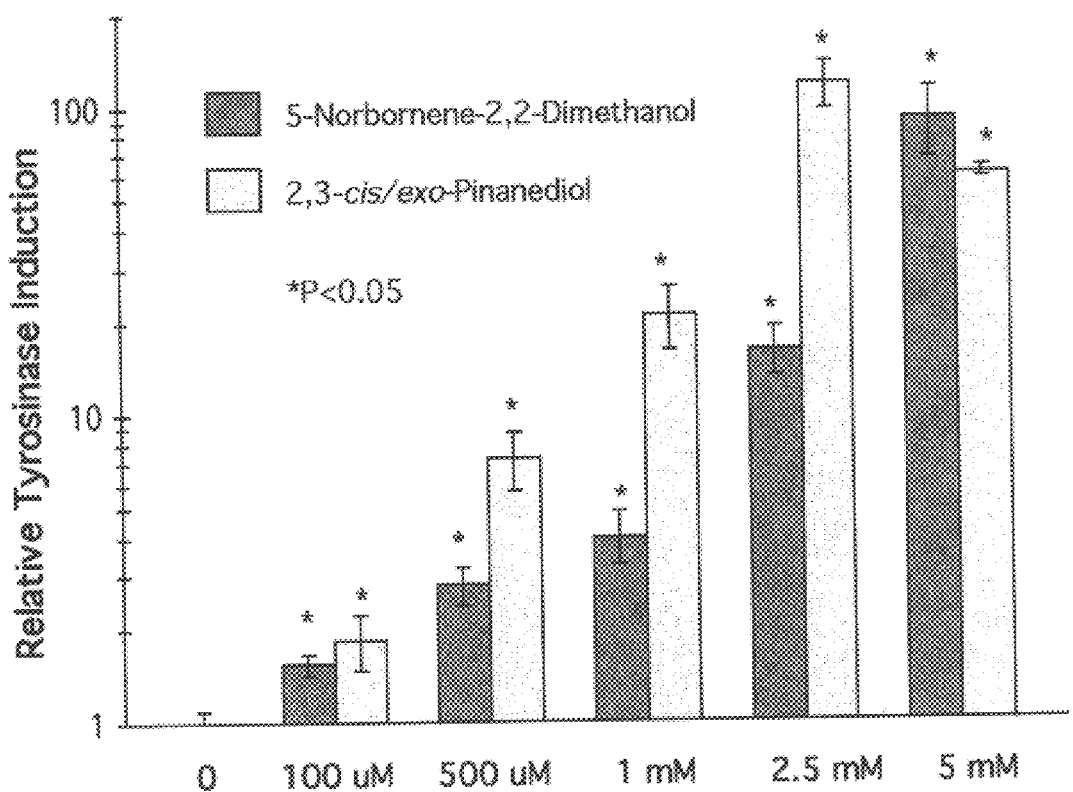
FIG. 4 is a series of bar graphs depicting the structure activity results obtained in Example 12.

In addition to being a more potent inducer of melanogenesis and nitric oxide (FIG. 4 and Table 17), 2,3-cis/exo-pinanediol was also a more potent inducer of cell cycle arrest than 5-norbornene-2,2-dimethanol (Table 17). As discussed in Example 2, induction of melanogenesis in association with cell cycle arrest is indicative of induction differentiation of melanoma cells. This indicates that 2,3-cis/exo-pinanediol may have even greater utility than 5-norbornene-2,2-dimethanol for use as a chemotherapeutic differentiation agent for treatment of melanoma and other types of cancers.

TABLE 17

|  | Cells (×10$^6$) | uM NO | nmoles NO/ 10$^6$ Cells |
|---|---|---|---|
| Untreated | 0.409 ± 0.037 | 1.74 ± 0.39 | 4.36 ± 1.16 |
| 1 mM 5-NBene-2,2-DM[1] | 0.423 ± 0.052 | 4.80 ± 0.32 | 11.6 ± 1.1* |
| 2.5 mM 5-NBene-2,2-DM | 0.269 ± 0.040* | 5.46 ± 0.32 | 21.4 ± 3.7* |
| 5 mM 5-NBene-2,2-DM | 0.090 ± 0.011* | 6.36 ± 0.12 | 72.9 ± 10.5* |
| 0.5 mM 2,3-cs/ex-PD[2] | 0.325 ± 0.002 | 3.54 ± 0.06 | 10.9 ± 0.2* |
| 1 mM 2,3-cs/ex-PD | 0.258 ± 0.010* | 6.36 ± 1.56 | 24.5 ± 5.4* |
| 2.5 mM 2,3-cs/ex-PD | 0.099 ± 0.014* | 12.6 ± 0.5 | 131 ± 15* |
| 5 mM 2,3-cs/ex-PD | 0.064 ± 0.006* | 11.0 ± 1.1 | 174 ± 15* |
| 85 mM ETOH[3] | 0.454 ± 0.036 | 3.18 ± 0.49 | 7.04 ± 1.00 |

[1]5-NBene-2,2-DM: 5-norbornene-2,2-dimethanol
[2]2,3-cs/ex-PD: 2,3-cis/exo-pinanediol ([1R,2R,3S,5R]-[-]-pinanediol)
[3]ETOH: ethanol solvent control for 5 mM 5-NBene-2,2-DM and 5 mM 2,3-cs/ex-PD (lower treatment concentrations received proportionally less ETOH)
*P < 0.05; T-test (X ± SE; n = 3)

EXAMPLE 13

Figure 5A:
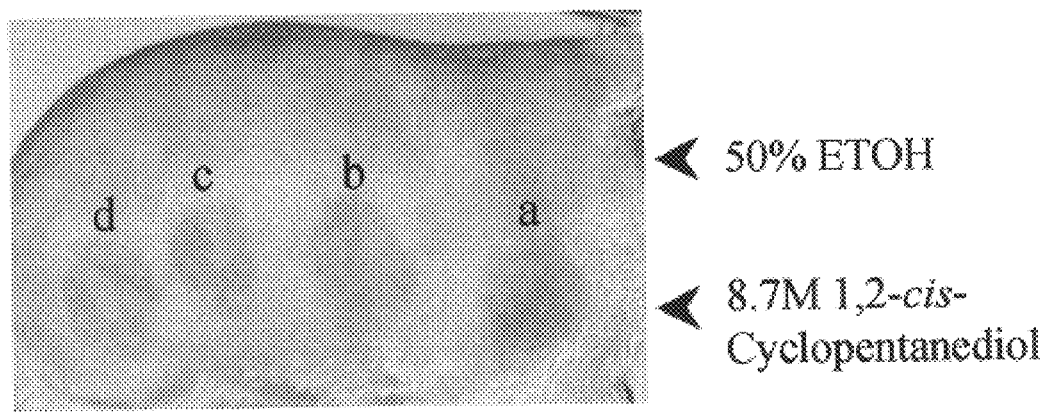
FIGS. 5A–5B are photographs of treated guinea pig skin as described in Example 13.
Figure 5B:
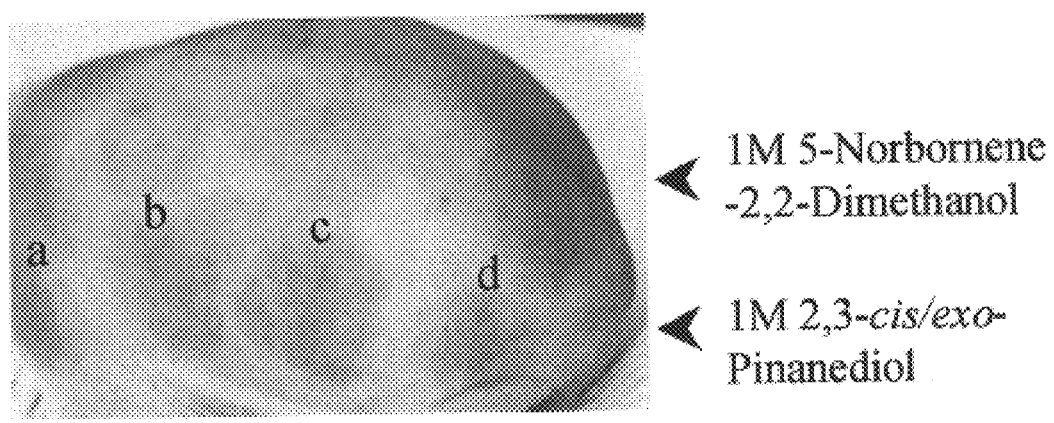

In studies using the guinea pig model identical to that described in Example 5, 2,3-cis/exo-pinanediol ([1R,2R,3S,5R]-[-]-pinanediol) exhibited 2- to 4-fold more melanogenic activity than equivalent concentrations of 5-norbornene-2,2-dimethanol when compared using treatment spots in the posterior half of animals (c and d in Table 18 and FIG. 5). In FIG. 5, a, b, c and d indicate treatment spots that transverse the anterior-posterior axis along the backs of guinea pigs. FIG. 5A, top row, shows spots a–d treated with 50% ETOH; FIG. 5A, bottom row, shows spots a–d treated with 8.7M 1,2-cis-cyclopentanediol in 20% ETOH; FIG. 5B, top row, shows spots a–d treated iwith 1M 5-norbornene-2,2-dimethanol in 8.5M propylene glycol, 20% ETOH, and 2% 2-pyrrolidone; and FIG. 5B, bottom row, shows spots a–d treated with 1M 2,3-cis/exo-pinanediol.

Figure 6A:
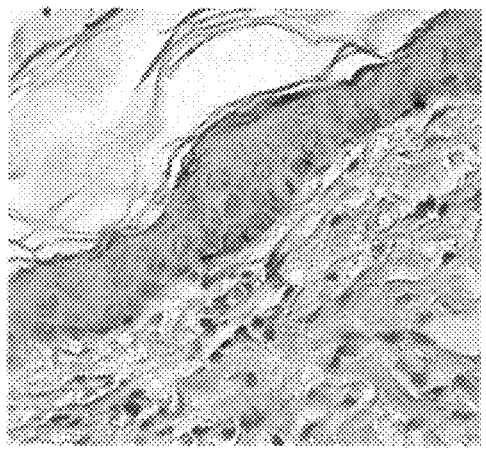
FIGS. 6A–6D are printouts as described in Example 13.
Figure 6B:
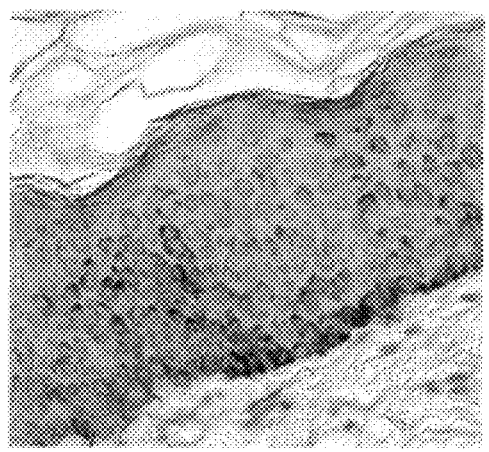
Figure 6C:
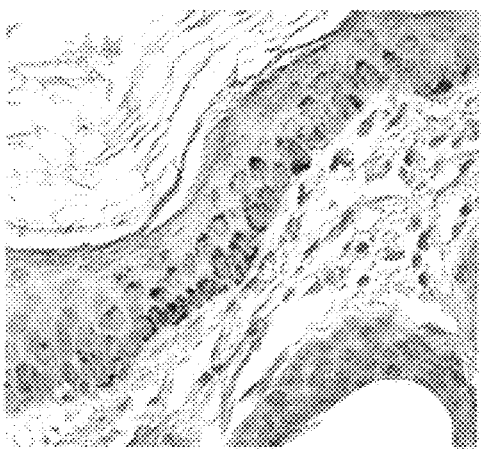
Figure 6D:
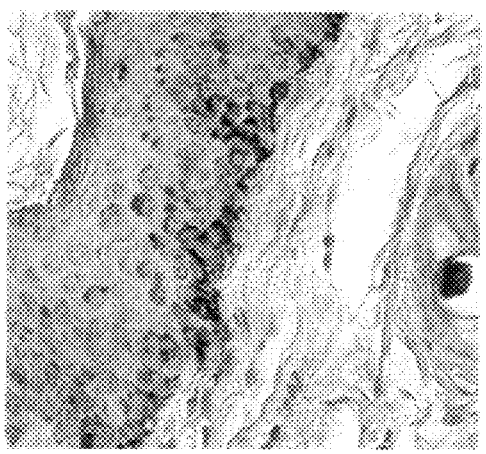

Whereas 5-norbornene-2,2-dimethanol required formulation in 8.5M propylene glycol with 2% 2-pyrrolidone to enable penetration of skin and induction of melanogenesis (see Example 5 and Tables 8 and 18), 2,3-cis/exo-pinanediol induced pigmentation when formulated in only 50% ethanol (Table 18). Biopsies show that similar to induction of melanogenesis by 1,2-cis-cyclopentanediol (FIGS. 1C and 6B) and 5-norbornene-2,2-dimethanol (FIGS. 1D and 6C), induction of melanogenesis by 2,3-cis/exo-pinanediol (FIG. 6D) was characterized by proliferation of melanocytes in the basal layer of the epidermis and distribution of melanin throughout the epidermis. Biopsies from skin treated with 50% ethanol (ETOH) exhibited no such response (FIG. 6A).

TABLE 18

Pigmentation Ratings[1] of Treated Spots Located Anterior (a) to Posterior (d) on Guinea Pigs

|  | a | b | c | d |
|---|---|---|---|---|
| 50% ETOH | 0.67 ± 0.12 | 0.25 ± 0.16 | 0.08 ± 0.08 | 0.04 ± 0.04 |
| 8.7 M 1,2-cis-CPD[2] | 1.83 ± 0.17* | 1.92 ± 0.43* | 1.92 ± 0.20* | 1.58 ± 0.24* |
| 1 M 5-NBene-2,2-DM[3] | 1.75 ± 0.43* | 1.25 ± 0.21* | 0.83 ± 0.15* | 0.29 ± 0.08* |
| 1 M 2,3-cs/ex PD[4] | 2.00 ± 0.20* | 1.75 ± 0.17* | 1.75 ± 0.17* | 1.04 ± 0.32* |

[1](X ± SE; n = 6); 0 = no change from background; +0.25 = slight darkening, indistinct; +0.5 = slight darkening; +1 = slight moderate darkening; +2 = moderate, even darkening; +3 = substantial, even darkening; +4 = profound, even darkening
[2]1,2-cis-cyclopentanediol in 20% ethanol (ETOH)
[3]5-norbornene-2,2-dimethanol in 8.5 M propylene glycol, 2% 2-pyrrolidone and 20% ETOH
[4]2,3-cis/exo-pinanediol ([1R,2R,3S,5R]-[-]-pinanediol) in 50% ETOH
*P < 0.05; Students T-test; significantly different from ETOH-treated site at same position on anterior-posterior axis

EXAMPLE 14

As a continuance of structure activity studies, a variety of pinanediol derivatives and related monocyclic derivatives were examined for melanogenic activity using the S91 cell line and procedures for analysis of tyrosinase described in Example 6. All of the compounds examined herein were either bicyclic- or monocyclic-monoterpenes (Table 19). In general, bicyclic-monoterpenes were more potent inducers of melanogenesis than monocyclic-monoterpenes, and within each of these groups, diols were more potent than alcohols, while non-hydroxylated compounds exhibited little or no activity (Table 19).

Bicyclic Monoterenes 1R,2R,3S,5R)-(-)-pinanediol was only slightly more potent than (1S,2S,3R,5S)-(+)-pinanediol (Table 19), indicating that melanogenic activity of 2,3-cis/exo-pinanediol is relatively independent of enantomeric configuration.

(1R)-(-)-trans-pinane-1,10-diol which contains a 2-hydroxymethyl group, exhibited melanogenic potency almost identical to that of (1R,2R,3S,5R)-(-)-pinanediol (Table 19). These results indicate that markedly different pinanediol structures may possess significant melanogenic activity. Therefore, all pinanediol compounds, including methanol and dimethanol substituted pinanediol derivatives are claimed in this invention.

(1S,2S,5S,)-2-hydroxy-3-pinanone was about half as potent as (1R,2R,3S,5R)-(-)-pinanediol (Table 19), indicating that substitution of a keto group for a hydroxyl group only partially reduces melanogenic activity. Given this finding, and the fact that keto groups may readily be converted to hydroxyl groups by chemical or biological lprocesses, it is contemplated that substitution of a keto group for a hydroxyl group in any of the compounds in this invention may result in retention of melanogenic activity. Therefore, all such keto-substituted compounds are claimed in this invention.

(-)-Isopinochampheol, an alcohol closely related to (1R,2R,3S,5R)-(-)-pinanediol (also known as [-]-2-hydroxyisopinocampheol), possessed considerably less melanogenic activity (Table 19). In addition, (-)-isopinochampheol resulted in detachment of cells from culture dishes at concentrations where (1R,2R,3S,5R)-(-)- pinanediol was a highly efficacious inducer of melanogenesis, indicating that the alcohol was more toxic than the diol. Similar results were obtained for (S)-cis-verbenol, another closely related bicyclic alcohol, and (1R)-(−)-myrtenol, a pinene derivative which contains a methanol substituent group (Table 19). Therefore, results for pinanediol derivatives indicate that alcohols are less potent inducers of melanogenesis than diols when tested in S91 cells, in agreement with previous results for norbornane derivatives (Example 6, FIG. 2).

However, as noted previously, although 2-norbornanemethanol exhibited considerably less melanogenic activity than 5-norbornene-2,2-dimethanol in S91 cells (Example 6, FIG. 2), it exhibited nearly equivalent cellular melanogenic activity in normal human epidermal melanocytes (Example 7, Table 12). Therefore, it is contemplated that similar findings may be incurred by (−)-isopinochampheol, (S)-cis-verbenol, (1R)-(−)-myrtenol, and related alcohols when tested in normal human epidermal melanocytes. Moreover, all alcohol derivatives of the compounds of this invention are either shown or contemplated to possess various degrees of melanogenic activity, and are therefore claimed in this invention. Nonsubstituted pinane enantiomers exhibited little or no lmelanogenic activity.

A mixture of 2,3-cis/exo- and 2,3-trans-bornanediol was found to exhibit approximately twice as much melanogenic activity as (1R,2R,3S,5R)-(−)-pinanediol (Table 19). Examination of purified stereoisomers indicated 2,3-cis/exo-bornanediol was more than twice as potent as 2,3-trans-bornanediol (Table 19). Borneol, an alcohol derivative, possessed much less activity (Table 19). Results for these bornane derivatives combined with those for the norbornane derivatives and pinane derivatives provide evidence that any bicyclic or multicyclic compound may provide a suitable framework for incorporation of substituent groups that induce melanogenesis. Therefore, all such compounds are claimed in this invention.

Within the bicyclic compounds that were examined, pinane and bornane derivatives (Table 19) were more potent inducers of melanogenesis than norbornane derivatives (Example 6, FIG. 2; Example 11, Tables 15 and 16). Unlike bicyclic norbornanes which contain no methyl substituents, the bicyclic-monoterpene pinanes and bornanes contain three methyl substituents. Thus, it is contemplated that a range of substituents including but not limited to methyl groups may increase melanogenic activity of bicyclic compounds.

Monocyclic Monoterpenes

Cis-p-menthane-3,8-diol and trans-p-menthane-3,8-diol were the most potent monocyclic monoterpenes examined (Table 19). However, these possessed much less melanogenic activity than any of the bicyclic-monoterpene diols examined (Table 19). Similar to results for the bicyclic-monoterpenes, the alcohols exhibited only low levels of melanogenic activity, and were toxic at the higher concentrations tested (Table 19). Moreover, R-(+)-limonene, a non-hydroxylated monocyclic-monterpene exhibited little or no melanogenic activity.

Similar to the monocyclic monoterpene alcohols, trans-p-menthane-2,8-diol exhibited much less melanogenic activity than cis-p-menthane-3,8-diol or trans-p-menthane-3,8-diol. However, unlike the alcohols, trans-p-menthane-2,8-diol was not toxic at the higher concentrations tested (Table 19). Thus, based on results for both bicyclic-monocyclic-monoterpenes, it is expected that diols will be preferable to alcohols as melanogenic agents, not only because they are more potent, but also because they appear to be less toxic.

Similar to cyclohexanediol, cis-p-menthane-3,8-diol and trans-p-menthane-3,8-diol possess six member rings. However, cis-p-menthane-3,8-diol and trans-p-menthane-3,8-diol are markedly more potent than either monocyclic hexanediol or pentanediol (Example 3 and Table 5). Thus, similar to bicyclic compounds, it is contemplated that a range of substituents including but not limited to methyl groups may increase melanogenic activity of monocyclic compounds. Enhancement of melanogenic potency of aliphatic diols by incorporation of methyl substituents has been demonstrated previously (e.g., compare 2,3-butanediol and 2,3-dimethyl-2,3-butanediol in Example 3, Table 5).

TABLE 19

Fold Induction of Tyrosinase Relative to Controls

| | 0.5 mM | 1 mM | 2.5 mM | 5 mM |
|---|---|---|---|---|
| Bicyclic Monoterpenes | | | | |
| (1R,2R,3S,5R)-(−)-pinanediol | 5.1 X | 17.6 X | 119 X | 50.6 X |
| (1S,2S,3R,5S)-(+)-pinanediol | ND[1] | 9.9 X | 68.4 X | 39.9 X |
| (1R)-(−)-trans-pinane-1,10-diol | ND | 14.3 X | 96.0 X | 36.8 X |
| (1S,2S,5S,)-2-hydroxy-3-pinanone | ND | 4.1 X | 37.1 X | 94.9 X |
| (−)-isopinocampheol | 2.3 X | 3.3 X | NA[2] | NA |
| (S)-cis-verbenol | 1.0 X | 3.0 X | 15.5 X | NA |
| (1R)-(−)-myrtenol[3] | 13.6 X | 17.6 X | 2.2 X | NA |
| (1R)-(+)-α-pinane | 1.2 X | 0.8 X | 0.9 X | NA |
| (1S)-(−)-α-pinane | 1.4 X | 1.1 X | 1.4 X | 1.2 X |
| 2,3-cis & trans-bornanediol | 9.9 X | 37.3 X | 99.7 X | ND |
| 2,3-cis/exo-bornanediol | 10.2 X | 28.5 X | 101 X | ND |
| 2,3-trans-bornanediol | 4.7 X | 12.8 X | 22.1 X | ND |
| borneol | 3.7 X | 2.1 X | 3.7 X | ND |
| Monocyclic Monoterpenes | | | | |
| cis-p-menthane-3,8-diol | 1.6 X | 3.0 X | 17.1 X | 11.6 X |
| trans-p-menthane-3,8-diol | 5.2 X | 13.2 X | 21.0 X | 7.3 X |
| sobrerol[4] | 1.8 X | 2.0 X | 2.3 X | 3.5 X |
| (−)-a-terpineol[5] | 6.2 X | 7.1 X | 4.7 X | NA |
| (1R,2S,5R)-(−)-menthol[6] | 2.0 X | 1.3 X | NA | NA |
| (1S,2R,5S)-(+)-menthol[7] | 0.7 X | 1.3 X | NA | NA |
| R-(+)-limonene[8] | 1.2 X | 1.8 X | 1.6 X | 1.4 X |

[1]ND: not done
[2]NA: not analyzed because cells had detached from culture dishes
[3](1R)-2-pinen-10-ol
[4]trans-p-menthene-2,8-diol
[5](S)-p-menth-1-en-8-ol
[6](1R,2S,5R)-2-isopropyl-5-methylcyclohexanol
[7](1S,2R,5S)-2-isopropyl-5-methylcyclohexanol
[8](+)-p-mentha-1,8-diene

We claim:

1. A composition for treating a skin proliferative disorder or a disorder of keratinization, which comprises:
   a) an effective amount of one or more of:
      (i) a saturated $C_7$ to $C_{50}$ diol having the following structure:

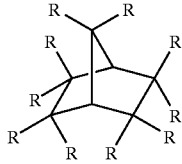 or 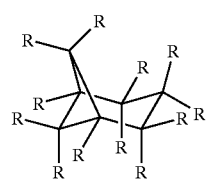

wherein
  each R is independently selected from $R_1$; $R_2$; hydroxyl, methyl, hydroxymethyl, —$(CH_2)_nCH_3$—, —$(CH_2)_n$OH, —$(CH_2)_nOR_1$, —$(CH_2)_n$—CH(OH)—CHOH, —$(CH_2)_n$—CH(OH)—CH(OH)$R_1$, —$(CH_2)_n$—CH(OH)—$(CH_2)_n$—$CH_2$(OH), —$(CH_2)_n$—CH(OH)—$(CH_2)_n$—CH(OH)$R_1$ or —$CH_2OR_1$, wherein each n is independently an integer from 0–25;
  each $R_1$ is independently selected from hydrogen; halogen; an acyl or amino acyl group containing from one atom to twenty atoms, at least one of which is carbon, nitrogen, oxygen, or sulfur; or a group containing from one atom to twenty atoms, one of which is carbon, nitrogen, oxygen, or sulfur, and
  $R_2$ is a linear, branched or unbranched, cyclic, bicyclic or polycyclic group containing from one atom to fifty atoms, at least one of which is carbon, nitrogen, oxygen, or sulfur; or
    (ii) an unsaturated $C_7$ to $C_{50}$ diol having the above structure; or
    (iii) a pharmaceutically acceptable salt or prodrug of (i); or
    (iv) a pharmaceutically acceptable salt or prodrug of (ii); and
  b) a suitable carrier.

2. The composition of claim 1, wherein the $C_7$ to $C_{50}$ diol is selected from the group consisting of:
  (a) 5-norbornen-2,2-dimethanol,
  (b) norbornane-2,2-dimethanol,
  (c) 2,3-norbornanediol (exo or endo or cis or trans),
  (d) 2,3-cis-exo-norbornanediol,
  (e) 2-(propyl-1,2-diol)-norbornane,
  (f) 2,7-norbornanediol,
  (g) 2-hydroxy-2-norbornanemethanol,
  (h) 1-(exo-2-norbornyl-)-propan-1,2-diol,
  (i) 1-(endo-2-norbornyl-)-propan-1,2-diol,
  (j) methyl-5-norbornene-2,3-dimethanol,
  (k) 2,3-cis/exo-pinanediol ([1R,2R,3S,5R]-[−]-pinanediol and [1S,2S,3R,5S]-[+]-pinanediol]),
  (l) (1R)-(−)-trans-pinane-1,10-diol,
  (m) 2,3-cis/exo-bornanediol,
  (n) 2,3-trans-bornanediol,
  (o) camphanediol,
  (p) camphenediol, and
  (q) 2,3-trans-pinanediol.

3. The composition of claim 1, wherein the disorder is selected from the group consisting of actinic keratosis, basal cell carcinoma, squamous cell carcinoma, fibrous histiocytoma, dermatofibrosarcoma protuberans, hemangioma, nevus flammeus, xanthoma, Kaposi's sarcoma, mastocytosis, mycosis fungoides, lentigo, nevocellular nevus, lentigo maligna, malignant melanoma, metastatic carcinoma, psoriasis vulgaris, psoriasis eosinophilia, and osteoma cutis.

4. The composition of claim 1 further comprising a penetration enhancer.

5. A composition for preventing a skin proliferative disorder or a disorder of keratinization, which comprises:
  a) an effective amount of one or more of:
    (i) a saturated $C_7$ to $C_{50}$ diol having the following structure:

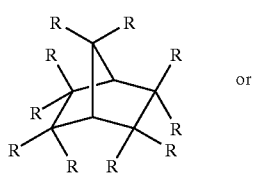 or 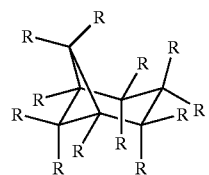

wherein
  each R is independently selected from $R_1$; $R_2$; hydroxyl, methyl, hydroxymethyl, —$(CH_2)_nCH_3$—, —$(CH_2)_n$OH, —$(CH_2)_nOR_1$, —$(CH_2)_n$—CH(OH)—CHOH, —$(CH_2)_n$—CH(OH)—CH(OH)$R_1$, —$(CH_2)_n$—CH(OH)—$(CH_2)_n$—$CH_2$(OH), —$(CH_2)_n$—CH(OH)—$(CH_2)_n$—CH(OH)$R_1$ or —$CH_2OR_1$, wherein each n is independently an integer from 0–25;
  each $R_1$ is independently selected from hydrogen; halogen; an acyl or amino acyl group containing from one atom to twenty atoms, at least one of which is carbon, nitrogen, oxygen, or sulfur; or a group containing from one atom to twenty atoms, one of which is carbon, nitrogen, oxygen, or sulfur, and
  $R_2$ is a linear, branched or unbranched, cyclic, bicyclic or polycyclic group containing from one atom to fifty atoms, at least one of which is carbon, nitrogen, oxygen, or sulfur; or
    (ii) an unsaturated $C_7$ to $C_{50}$ diol having the above structure; or
    (iii) a pharmaceutically acceptable salt or prodrug of (i); or
    (iv) a pharmaceutically acceptable salt or prodrug of (ii); and
  b) a suitable carrier.

6. The composition of claim 5, wherein the $C_7$ to $C_{50}$ diol is selected from the group consisting of:
  (a) 5-norbornen-2,2-dimethanol,
  (b) norbornane-2,2-dimethanol,
  (c) 2,3-norbornanediol (exo or endo or cis or trans),
  (d) 2,3-cis-exo-norbornanediol,
  (e) 2-(propyl-1,2-diol)-norbornane,
  (f) 2,7-norbornanediol,
  (g) 2-hydroxy-2-norbornanemethanol,
  (h) 1-(exo-2-norbornyl-)-propan-1,2-diol,
  (i) 1-(endo-2-norbornyl-)-propan-1,2-diol,
  (j) methyl-5-norbornene-2,3-dimethanol,
  (k) 2,3-cis/exo-pinanediol ([1R,2R,3S,5R]-[−]-pinanediol and [1S,2S,3R,5S]-[+]-pinanediol]),
  (l) (1R)-(−)-trans-pinane-1,10-diol,
  (m) 2,3-cis/exo-bornanediol,
  (n) 2,3-trans-bornanediol,
  (o) camphanediol,
  (p) camphenediol, and
  (q) 2,3-trans-pinanediol.

7. The composition of claim 5 further comprising a penetration enhancer.

8. The composition of claim 5, wherein the disorder is selected from the group consisting of actinic keratosis, basal cell carcinoma, squamous cell carcinoma, fibrous histiocytoma, dermatofibrosarcoma protuberans, hemangioma, nevus flammeus, xanthoma, Kaposi's sarcoma, mastocytosis, mycosis fungoides, lentigo, nevocellular nevus, lentigo maligna, malignant melanoma, metastatic carcinoma, psoriasis vulgaris, psoriasis eosinophilia, and osteoma cutis.

9. A composition for increasing the melanin content of mammalian melanocytes, which comprises:
  a) an effective amount of one or more of:
    (i) a saturated $C_7$ to $C_{50}$ diol having the following structure:

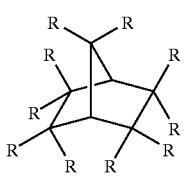 or 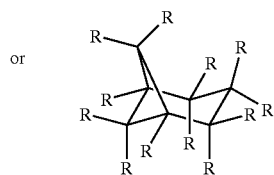

wherein
each R is independently selected from $R_1$; $R_2$; hydroxyl, methyl, hydroxymethyl, —$(CH_2)_nCH_3$—, —$(CH_2)_nOH$, —$(CH_2)_nOR_1$, —$(CH_2)_n$—CH(OH)—CHOH, —$(CH_2)_n$—CH(OH)—CH(OH)$R_1$, —$(CH_2)_n$—CH(OH)—$(CH_2)_n$—$CH_2$(OH), —$(CH_2)_n$—CH(OH)—$(CH_2)_n$—CH(OH)$R_1$ or —$CH_2OR_1$, wherein each n is independently an integer from 0–25;
each $R_1$ is independently selected from hydrogen; halogen; an acyl or amino acyl group containing from one atom to twenty atoms, at least one of which is carbon, nitrogen, oxygen, or sulfur; or a group containing from one atom to twenty atoms, one of which is carbon, nitrogen, oxygen, or sulfur, and
$R_2$ is a linear, branched or unbranched, cyclic, bicyclic or polycyclic group containing from one atom to fifty atoms, at least one of which is carbon, nitrogen, oxygen, or sulfur; or
(ii) an unsaturated $C_7$ to $C_{50}$ diol having the above structure; or
(iii) a pharmaceutically acceptable salt or prodrug of (i); or
(iv) a pharmaceutically acceptable salt or prodrug of (ii); and
b) a suitable carrier.

10. The composition of claim 9, wherein the $C_7$ to $C_{50}$ diol is selected from the group consisting of:
(a) 5-norbornen-2,2-dimethanol,
(b) norbornane-2,2-dimethanol,
(c) 2,3-norbornanediol (exo or endo or cis or trans),
(d) 2,3-cis-exo-norbornanediol,
(e) 2-(propyl-1,2-diol)-norbornane,
(f) 2,7-norbornanediol,
(g) 2-hydroxy-2-norbornanemethanol,
(h) 1-(exo-2-norbornyl-)-propan-1,2-diol,
(i) 1-(endo-2-norbornyl-)-propan-1,2-diol,
(j) methyl-5-norbornene-2,3-dimethanol,
(k) 2,3-cis/exo-pinanediol ([1R,2R,3S,5R]-[−]-pinanediol and [1S,2S,3R,5S]-[+]-pinanediol]),
(l) (1R)-(−)-trans-pinane-1,10-diol,
(m) 2,3-cis/exo-bornanediol,
(n) 2,3-trans-bornanediol,
(o) camphanediol,
(p) camphenediol, and
(q) 2,3-trans-pinanediol.

11. The composition of claim 9 further comprising a penetration enhancer.

12. A method for treating a skin proliferative disorder or a disorder of keratinization in a mammal comprising administering to a mammal in need of such treatment an effective amount of the composition of claim 1.

13. The method of claim 12 wherein the composition further comprises a penetration enhancer.

14. A method for preventing a skin proliferative disorder or a disorder of keratinization in a mammal comprising administering to a mammal in need of such preventive treatment an effective amount of the composition of claim 5.

15. The method of claim 14 wherein the composition further comprises a penetration enhancer.

16. A method for increasing the melanin content of mammalian melanocytes comprising administering to said melanocytes an effective amount of the composition of claim 9.

17. The method of claim 16 wherein the composition further comprises a penetration enhancer.

18. A composition for treating a skin proliferative disorder or a disorder of keratinization, which comprises:
a) an effective amount of one or more of:
(i) 2,3-cis/exo-pinanediol ([1R,2R,3S,5R]-[<]-pinanediol and [1S,2S,3R,5S]-[+]-pinanediol]); or
(ii) a pharmaceutically acceptable salt or prodrug of (i); and
b) a suitable carrier.

19. The composition of claim 18 further comprising a penetration enhancer.

20. A method for treating a skin proliferative disorder or a disorder of keratinization in a mammal comprising administering to a mammal in need of such treatment an effective amount of the composition of claim 18.

21. The method of claim 20 wherein the composition further comprises a penetration enhancer.

22. A composition for preventing a skin proliferative disorder or a disorder of keratinization, which comprises:
a) an effective amount of one or more of:
(i) 2,3-cis/exo-pinanediol ([1R,2R,3S,5R]-[<]-pinanediol and [1S,2S,3R,5S]-[+]-pinanediol]); or
(ii) a pharmaceutically acceptable salt or prodrug of (i); and
b) a suitable carrier.

23. The composition of claim 22 further comprising a penetration enhancer.

24. A method for preventing a skin proliferative disorder or a disorder of keratinization in a mammal comprising administering to a mammal in need of such preventive treatment an effective amount of the composition of claim 22.

25. The method of claim 24 wherein the composition further comprises a penetration enhancer.

26. A composition for increasing the melanin content of mammalian melanocytes, which comprises:
a) an effective amount of one or more of:
(i) 2,3-cis/exo-pinanediol ([1R,2R,3S,5R]-[<]-pinanediol and [1S,2S,3R,5S]-[+]-pinanediol]); or
(ii) a pharmaceutically acceptable salt or prodrug of (i); and
b) a suitable carrier.

27. The composition of claim 26 further comprising a penetration enhancer.

28. A method for increasing the melanin content of mammalian melanocytes comprising administering to said melanocytes an effective amount of the composition of claim 26.

29. The method of claim 28 wherein the composition further comprises a penetration enhancer.

30. A composition for treating a skin proliferative disorder or a disorder of keratinization, which comprises:
a) an effective amount of one or more of:
(i) 2,3-cis/exo-pinanediol; or
(ii) a pharmaceutically acceptable salt or prodrug of (i); and
b) a suitable carrier.

31. The composition of claim 30 further comprising a penetration enhancer.

32. A method for preventing a skin proliferative disorder or a disorder of keratinization in a mammal comprising administering to a mammal in need of such treatment an effective amount of the composition of claim 30.

33. The method of claim 32 wherein the composition further comprises a penetration enhancer.

34. A composition for treating a skin proliferative disorder or a disorder of keratinization, which comprises:
   a) an effective amount of one or more of:
      (i) 2,3-cis/exo-pinanediol; or
      (ii) a pharmaceutically acceptable salt or prodrug of (i); and
   b) a suitable carrier.

35. The composition of claim 34 further comprising a penetration enhancer.

36. A method for preventing a skin proliferative disorder or a disorder of keratinization in a mammal comprising administering to a mammal in need of such preventivetreatment an effective amount of the composition of claim 34.

37. The method of claim 36 wherein the composition further comprises a penetration enhancer.

38. A composition for increasing the melanin content of mammalian melanocytes, which comprises:
   a) an effective amount of one or more of:
      (i) 2,3-cis/exo-pinanediol; or
      (ii) a pharmaceutically acceptable salt or prodrug of (i); and
   b) a suitable carrier.

39. The composition of claim 38 further comprising a penetration enhancer.

40. A method for increasing the melanin content of mammalian melanocytes comprising administering to said melanocytes an effective amount of the composition of claim 38.

41. The method of claim 40 wherein the composition further comprises a penetration enhancer.

* * * * *

UNITED STATES PATENT AND TRADEMARK OFFICE
CERTIFICATE OF CORRECTION

PATENT NO.       : 6,623,724 B2
APPLICATION NO.  : 09/085917
DATED            : September 23, 2003
INVENTOR(S)      : David A. Brown et al.

It is certified that error appears in the above-identified patent and that said Letters Patent is hereby corrected as shown below:

Column 27/line 26 "5-norbornen" should read --5-norbornene--

Column 28/line 26 "5-norbornen" should read --5-norbornene--

Column 29/line 29 "5-norbornen" should read --5-norbornene--

Column 30/line 6 "[ < ]" should read --[ - ]--

Column 30/line 22 "[ < ]" should read --[ - ]--

Column 30/line 39 "[ < ]" should read --[ - ]--

Column 30/line 56 "-pinanediol" should read -- -bornanediol--

Column 31/line 4 "-pinanediol" should read -- -bornanediol--

Column 31/line 12 "preventivetreat-" should read --preventive treat- --

Column 32/line 2 "-pinanediol" should read -- -bornanediol--

Signed and Sealed this

Eighth Day of May, 2007

JON W. DUDAS
*Director of the United States Patent and Trademark Office*